United States Patent [19]

Pate et al.

[11] Patent Number: 5,631,297
[45] Date of Patent: May 20, 1997

[54] ANANDAMIDES USEFUL FOR THE TREATMENT OF INTRAOCULAR HYPERTENSION, OPHTHALMIC COMPOSITIONS CONTAINING THE SAME AND METHODS OF USE OF THE SAME

[76] Inventors: David W. Pate, Postbus 1397, 1000 BJ Amsterdam, Netherlands; Tomi Jarvinen; Kristiina Jarvinen, both of Sompatie 3 Cl, Fin-70200 Kuopio, Finland; Arto Urtti, 8 Whittier Ct., Mill Valley, Calif. 94941

[21] Appl. No.: 272,532

[22] Filed: Jul. 11, 1994

[51] Int. Cl.$^6$ .................................................. A61K 31/16
[52] U.S. Cl. .................... 514/627; 514/625; 514/628; 514/629; 514/528; 514/913; 514/912
[58] Field of Search ............................ 514/912, 625, 514/627, 628, 629, 528, 913

[56] References Cited

U.S. PATENT DOCUMENTS

| | | | |
|---|---|---|---|
| 3,649,650 | 3/1972 | Razdan et al. | 260/345.3 |
| 4,327,028 | 4/1982 | Kaplan | 260/345.3 |
| 4,474,811 | 10/1984 | Masuda et al. | 424/317 |
| 4,476,140 | 10/1984 | Sears et al. | 424/283 |
| 4,983,586 | 1/1991 | Bodor | 514/58 |
| 5,070,081 | 12/1991 | Majid et al. | 514/58 |
| 5,418,225 | 5/1995 | Javitt et al. | 514/58 |

FOREIGN PATENT DOCUMENTS

| | | | |
|---|---|---|---|
| 0326196 | 8/1989 | European Pat. Off. | A61K 31/575 |
| 0400637 | 12/1990 | European Pat. Off. | A61K 37/02 |
| 0435682 | 7/1991 | European Pat. Off. | A61K 31/557 |
| 0472327 | 2/1992 | European Pat. Off. | A61K 31/535 |
| WO94/12466 | 6/1994 | WIPO | C07C 233/00 |

OTHER PUBLICATIONS

Felder et al., "Anandamide, an Endogenous Cannabimimetic Eicosanoid, Binds to the Clone Human . . . ", *Proc. Natl. Acad. Sci USA* 90:7656–7660 (1993).

Hanus et al, "Two New Unsaturated Fatty Acid Ethanolamides in Brain That Bind to the Cannabinoid Receptor", *J. Med. Chem.*, 36:3032–3034 (1993).

Devane et al, "Isolation and Structure of a Brain Constituent That Binds to the Cannabinoid Receptor", *Science*, 258:1946–1949 (1992).

Devane et al, "A Novel Probe for the Cannabinoid Receptor", *J. Med. Chem.*, 35:2065–2069 (1992).

Matsuda et al, "Structure of a Cannabinoid Receptor and Functional Expression of the Cloned cDNA", *Nature*, 346:561–564 (1990).

Cooler et al, "Effect of Delta-9-Tetrahydrocannabinol on Intraocular Pressure in Humans", *Southern Medical Journal*, 70(8):951–954 (1977).

Hefler et al, "Marihuana Smoking and Intraocular Pressure", *JAMA*, 217(10):1392 (1971).

International Cannabis Research Society, 1993 Meeting, Abstracts, pp. 1–2, 9, 14, 23, 29 and 42, Scarborough, Ontario, Canada, Jun. 11–12, 1993.

*Primary Examiner*—C. Warren Ivy
*Assistant Examiner*—Rosalynd Williams
*Attorney, Agent, or Firm*—Sughrue, Mion, Zinn, Macpeak & Seas

[57] ABSTRACT

Anandamides useful for the treatment of intraocular hypertension, as well as ophthalmic compositions comprising the same and a cyclodextrin, and methods of use of these compounds to treat intraocular hypertension.

29 Claims, 12 Drawing Sheets

ANANDAMIDES USEFUL FOR THE TREATMENT OF INTRAOCULAR HYPERTENSION, OPHTHALMIC COMPOSITIONS CONTAINING THE SAME AND METHODS OF USE OF THE SAME

FIELD OF THE INVENTION

The present invention relates to anandamides useful for the treatment of intraocular hypertension, as well as ophthalmic compositions comprising the same and a cyclodextrin, and methods of use of said compositions to treat intraocular hypertension.

BACKGROUND OF THE INVENTION

Subjects who smoke marijuana have reduced intraocular pressure (Helper et al, *J. Am. Med. Assoc.*, 217: 1392 (1971)). The primary psychoactive ingredient in marijuana is known to be delta-9-tetrahydrocannabinol ("THC"). Human experiments involving intravenous administration of pure THC have confirmed the intraocular pressure reduction phenomenon seen with subjects who smoke marijuana (Cooler et al, *South. Med. J.*, 70: 954 (1977)). As a result, cannabinoids have been investigated as anti-glaucoma agents.

However, use of systemic cannabinoids, such as THC, as anti-glaucoma agents is disadvantageous since they can cause significant adverse psychological and physiological side-effects. In addition, cannabinoids are lipophilic compounds that are very insoluble in water, thus hindering their application as topical ophthalmic pharmaceutical products.

Anandamides are structurally different from cannabinoids, such as THC. The first anandamide discovered (Devane et al, *Science*, 258: 1946 (1992)) is represented by the following formula, and is known as arachidonylethanolamide:

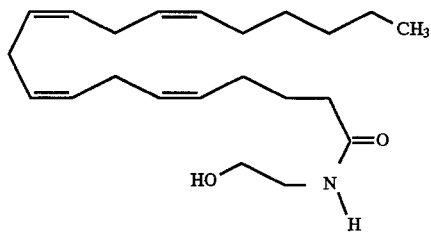

Two other endogenous anandamides were subsequently discovered (Hanus et al, *J. Med. Chem.*, 36: 3032 (1993)). Several synthetic analogs have also been made (Felder et al, *Proc. Natl. Acad. Sci. USA*, 90: 7656 (1993)).

Arachidonylethanolamide is an endogenous porcine ligand reported to bind to the cannabinoid receptor in the brain (Devane et al, supra). It was therefore postulated in the present invention, that like THC, anandamides might be useful in reducing intraocular pressure.

Aqueous eyedrops are the most commonly used dosage form for ophthalmic drug delivery. This is because eyedrops are relatively easy to use, relatively inexpensive and do not impair vision. However, the aqueous solubility of anandamides is very poor. Thus, ophthalmic delivery of anandamides in aqueous eyedrops is difficult.

Anandamides are soluble in oil solutions (e.g., castor oil, sesame oil, mineral oil, etc.) and organic solvents (e.g., ethanol, chloroform, etc.). However, these solvents cause harmful side-effects when administered to the eyes. Thus, they are generally not used for ophthalmic drug delivery.

Cyclodextrins ("CDs") are a group of homologous cyclic oligosaccharides consisting of six, seven or eight glucopyranose units, and are respectively called α-, β- or γ-cyclodextrin. It is generally known that CDs can form inclusion complexes with various hydrophobic organic or inorganic compounds, and as a result, increase the solubility or stability of these compounds (Bekers et al, *Drug Dev. Ind. Pharm.*, 17: 1503–1549 (1991); and Duchene et al, *Drug Dev. Ind. Pharm.*, 16: 2487–2499 (1990)). CDs have also been used to increase the dissolution rate, as well as the bioavailability of various drugs, and to decrease the toxicity of topically applied drugs (Bekers et al, *Drug Dev. Ind. Pharm.*, 17: 1503–1549 (1991)).

CDs can be regarded as cone-shaped molecules, where the polar hydroxyl groups of the glucose unit are oriented towards the outside of the structure (Bekers et al, *Drug Dev. Ind. Pharm.*, 17: 1503–1549 (1991)). Therefore, the outside of CDs is hydrophilic, whereas the inside of the cavity is hydrophobic in character. The minimum requirement for inclusion complex formation is that the guest molecule must fit, entirely or at least partially, into the CD cavity (Bekers et al, *Drug Dev. Ind. Pharm.*, 17: 1503–1549 (1991)).

However, little attention had been paid to the suitability of CDs for use with drugs having ophthalmic activity or for use in ophthalmic compositions. Co-administered CD has increased the ocular absorption of dexamethasone (Loftsson et al, *Int. J. Pharm.*, 104: 181–184 (1994), dexamethasone acetate (Usayapant et al, *Pharm. Res.*, 8: 1495–1499 (1991) and pilocarpine (Freedman et al, *Curr. Eye Res.*, 12: 641–647 (1993), and the intraocular pressure lowering effect of carbonic anhydrase inhibitors (Loftsson et al, *Eur. J. Pharm. Sci.*, 1: 175–180 (1994) (see also EP 326196B1, EP 400637A3, EP 435682A2 and EP 472327A1).

SUMMARY OF THE INVENTION

Accordingly, an object of the present invention is to provide compounds useful for the treatment of elevated intraocular pressure (IOP).

Another object of the present invention is to provide an ophthalmic composition useful for the reduction of IOP which is delivered non-systemically to the site of action, thereby enhancing the effect on IOP and minimizing entry into the central nervous system.

A further object of the present invention is to provide a method for reducing IOP using said compounds.

These and other objects of the present invention, which will be apparent from the detailed description of the invention provided hereinafter, have been met, in a one embodiment, by anandamides represented by Formula (I):

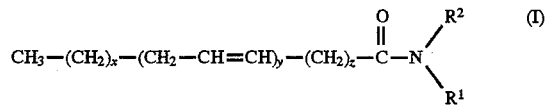

wherein $R^1$ and $R^2$ are each H or $(CH_2)_a$-$(R^4CH)_b$—$(CH_2)_c$-$R^3$, wherein a, b and c are each an integer of from 0 to 10, preferably 1 to 4; and $R^3$ is OH, SH, $CH_3$, $CH=CH_2$, C≡CH, C≡N, F, Cl, Br or I, preferably OH, SH or F, more preferably OH; $R^4$ is H or $(CH_2)_l$—$CH_3$, wherein l is an integer from 0 to 10, preferably 0 to 4; provided that a+b+c+l≦10, preferably ≦4, preferably one of $R^1$ and $R^2$ is H and the other of $R^1$ and $R^2$ is $(CH_2)_a$-$(R^4CH)_b$—$(CH_2)_c$-$R^3$;

x is an integer of from 0 to 18, preferably 2 to 5;

y is an integer of from 0 to 8, preferably 2 to 4; and z is an integer of from 0 to 18, preferably 2 to 5.

In another embodiment, the above-described objects have been met by an ophthalmic composition for reducing intraocular pressure comprising an admixture of a pharmaceutically effective amount of a compound represented by Formula (I), and a cyclodextrin.

In still another embodiment, the above-described objects have been met by a method for treatment of intraocular hypertension comprising topically administering a pharmaceutically effective amount of a compound represented by Formula (I) to an affected eye in need of such treatment.

DETAILED DESCRIPTION OF THE INVENTION

Figure 1A:
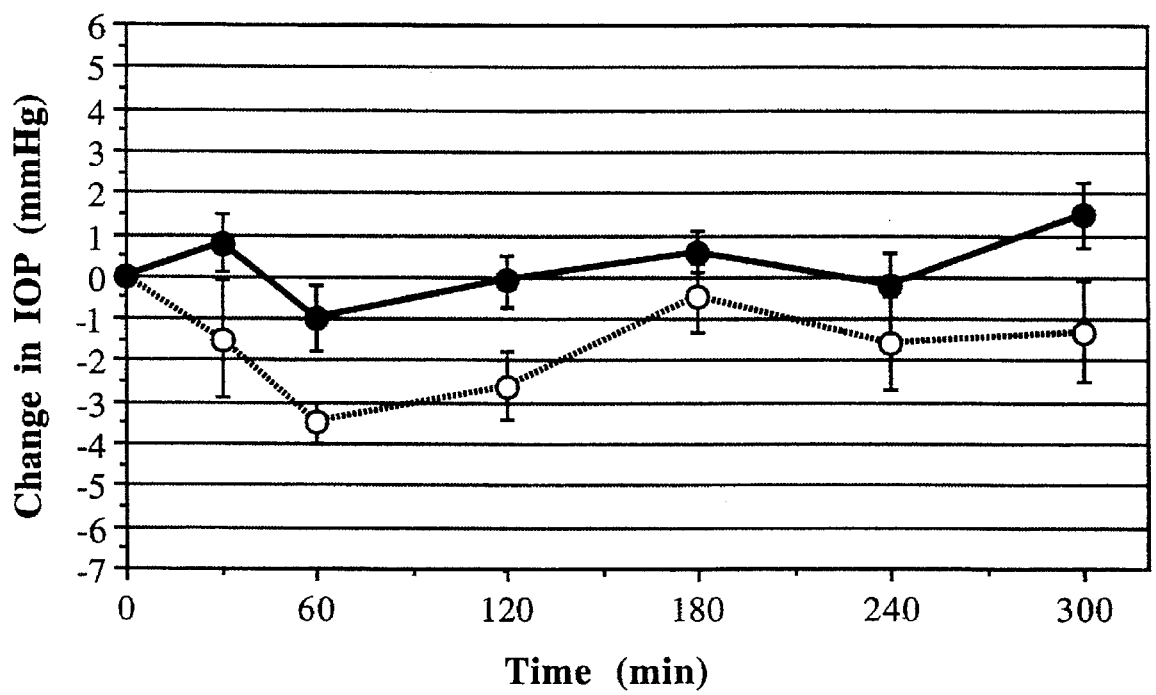
FIG. 1A shows the intraocular pressure ("IOP") changes in normotensive pigmented rabbits (treated eyes) after unilateral ocular administration (25 μl) of 0.125% (w/v) arachidonylethanolamide (o) or 0.9% (w/v) NaCl (●), mean ± S.E. (n=6).

As discussed above, anandamides of the present invention are represented by Formula (I):

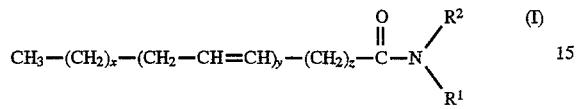

wherein $R^1$ and $R^2$ are each H or $(CH_2)_a$-$(R^4CH)_b$—$(CH_2)_c$-$R^3$, wherein a, b and c are each an integer of from 0 to 10, preferably 1 to 4; and $R^3$ is OH, SH, $CH_3$, $CH=CH_2$, $C\equiv CH$, $C\equiv N$, F, Cl, Br or I, preferably OH, SH or F, more preferably OH; $R^4$ is H or $(CH_2)_l$—$CH_3$, wherein l is an integer from 0 to 10, preferably 0 to 4; provided that $a+b+c+l+\leq 10$, preferably $\leq 4$, preferably one of $R^1$ and $R^2$ is H and the other of $R^1$ and $R^2$ is $(CH_2)_a$-$(R^4CH)_b$—$(CH_2)_c$-$R^3$;

X is an integer of from 0 to 18, preferably 2 to 5;

y is an integer of from 0 to 8, preferably 2 to 4; and z is an integer of from 0 to 18, preferably 2 to 5.

Specific non-limiting examples of the compounds represented by Formula (I) which can be employed in the present invention include the following:

arachidonylethanolamide (Devane et al, supra)

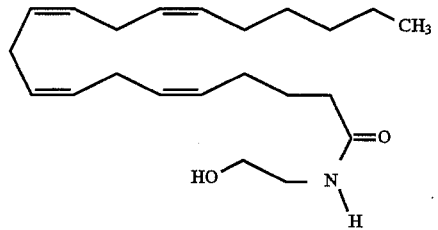

Formula (I):
$R^1$=$(CH_2)_a$-$(R^4CH)_b$—$(CH_2)_c$-$R^3$; $R^2$ =H; $R^3$=OH;
$R^4$=H; a=0; b=2; c=0; x=3; y=4; and
z=3.

arachidonylethanethiolamide

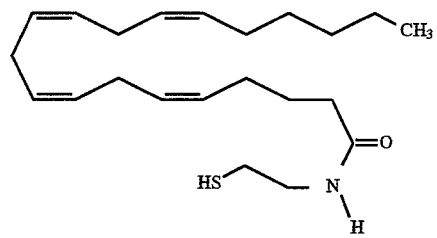

Formula (I):
$R^1$=$(CH_2)_a$-$(R^4CH)_b$—$(CH_2)_c$-$R^3$; $R^2$=H; $R^3$=SH;
$R^4$=H; a=0; b=2; c=0; x=3; y=4; and
Z=3.

arachidonylfluoroethylamide (Ryan et al, Proc. Int. Cannabis Res. Soc. Meet., Toronto, Canada, Jun. 11–12, 1993, page 2)

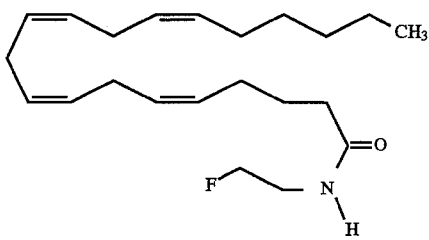

Formula (I):
$R^1$ $(CH_2)_a$-$(R^4CH)_b$—$(CH_2)_c$-$R^3$; $R^2$=H; $R^3$=F;
$R^4$=H; a=0; b=2; c=0; x=3; y=4; and
Z=3.

8,11,14-eicosatrienylethanolamide (Felder et al, supra)

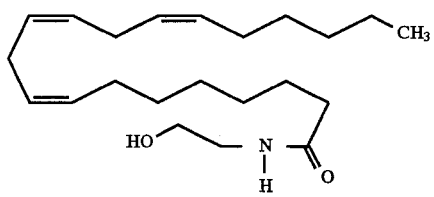

Formula (I):
$R^1(CH_2)_a$-$(R^4CH)_b$—$(CH_2)_c$-$R^3$; $R^2$=H; $R^3$=OH;
$R^4$=H; a=0; b=2; c=0; x=3; y=3; and
Z=6.

arachidonylpropanolamide (Felder et al, supra)

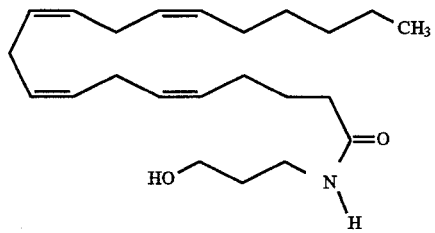

Formula (I):
$R^1(CH_2)_a$-$R^4CH)_b$—$(CH_2)_c$-$R^3$; $R^2$=H; $R^3$=OH;
$R^4$=H; a=0; b=3; c=0; x=3; y=4; and
z=3.

7,10,13,16-docosatetraenylethanolamide (Felder et al, supra)

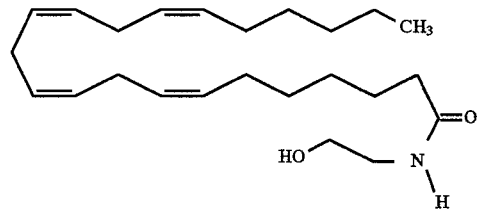

Formula (I):
$R^1$=$(CH_2)_a$-$(R^4CH)_b$—$(CH_2)_c$-$R^3$; $R^2$=H; $R^3$=OH;
$R^4$=H; a=0; b=2; c=0; x=3; y=4; and
z=5.

Additional examples of compounds within the scope of Formula (I) which can be employed in the present invention include:

Palmatidylethanolamide, which is described by Felder et al, supra, and is a compound of Formula (I), wherein
$R^1=(CH_2)_a$-$(R^4CH)_b$—$(CH_2)_c$-$R^3$; $R^2$=H; $R^3$=OH; $R^4$=H; a=0; b=2; c=0; x=7; y=0; and z=7.

4,7,10,13,16,19-Docosahexaenylethanolamide, which is described by Felder et al, supra, and is a compound of Formula (I), wherein
$R^1=(CH_2)_a$-$(R^4CH)_b$—$(CH_2)_c$-$R^3$; $R^2$=H; $R^3$=F; $R^4$=H; a=0; b=2; c=0; x=0; y=6; and z=2.

Arachidylfluoroethylamide, which is described by Ryan et al, supra, and is a compound of Formula (I), wherein
$R^1=(CH_2)_a$-$(R^4CH)_b$—$(CH_2)_c$-$R^3$; $R^2$=H; $R^3$=F; $R^4$=H; a=0; b=2; c=0; x=9; y=0; and z=9.

Arachidonylamide, which is described by Felder et al, supra, and is a compound of Formula (I), wherein
$R^1$=H; $R^2$=H; x=3; y=4; and z=3.

Arachidonyl-1-methyl-ethanolamide, which is described by Felder et al, supra, and is a compound of Formula (I), wherein
$R^1=(CH_2)_a$-$(R^4CH)_b$—$(CH_2)_c$-$R^3$; $R^2$=H; $R^3$=OH; $R^4=(CH_2)_l$—$CH_3$; a=1; b=1; c=0; l=0; x=3; y=4; and z=3.

Arachidonyl-2-methyl-ethanolamide, which is described by Felder et al, supra, and is a compound of Formula (I), wherein
$R^1=(CH_2)_a$-$(R^4CH)_b$—$(CH_2)_c$-$R^3$; $R^2$=H; $R^3$=OH; $R^4=(CH_2)_l$—$CH_3$; a=0; b=1; c=1; l=0; x=3; y=4; and z=3.

Gamma-linolenylethanolamide, which is described by Felder et al, supra, and is a compound of Formula (I), wherein
$R^1(CH_2)_a$-$(R^4CH)_b$—$(CH_2)_c$-$R^3$; $R^2$=H; $R^3$=OH; a=1; b=0; c=1; x=3; y=3; and z=4.

Linoleylethanolamide, which is described by Hanus et al, supra, and is a compound of Formula (I), wherein
$R^1=(CH_2)_a$-$(R^4CH)_b$—$(CH_2)_c$-$R^3$; $R^2$=H; $R^3$=OH; a=1; b=0; c=1; x=3; y=2; and z=7.

All of the compounds within Formula (I) can be synthesized according to the methods of Devane et al, *Science*, 258: 1946 (1992), by utilizing the appropriate fatty acid chloride and amine precursors.

In the present invention, the insolubility of the compounds represented by Formula (I) in aqueous solutions has been overcome by the admixture thereof with CDs which do not cause harmful ocular side-effects in patients.

Due to their hydrophilic character and size, CDs are not transported through the cell membranes (Frijlink et al, *Int. J. Pharm.*, 64: 195–205 (1990); and Nakanishi et al, *Chem. Pharm. Bull.*, 37: 1395–1398 (1989)). In addition, CDs have low general toxicity, and only small amounts are necessary to administer in topical ophthalmic compositions (Doorne, *Eur. J. Pharm. Biopharm.*, 39: 133–139 (1993)). For these reasons, little or no side-effects are observed after topical intraocular administration. Thus, CDs demonstrate great utility as useful adjuvants in the ophthalmic compositions of the present invention.

Examples of the cyclodextrin which can be employed in the ophthalmic compositions of the present invention include α-cyclodextrins, β-cyclodextrins and γ-cyclodextrins, and derivatives thereof, such as cyclodextrin ethers (alkyl, e.g., methyl and ethyl, ethers or hydroxyalkyl, e.g., hydroxyethyl and hydroxypropyl, ethers) and esters (acylates, sulfonates, sulfates and phosphates). For ease of use (inclusion efficiency), economical reasons and commercial availability, the cyclodextrin is preferably a β-cyclodextrin, more preferably a β-cyclodextrin alkylated or hydroxyalkylated in the 2-, 3- and/or 6-position. Particularly useful β-cyclodextrins include 2-hydroxypropyl-β-cyclodextrin and heptakis-(2,6-di-O-methyl)-β-cyclodextrin.

The amount of compound represented by Formula (I) to be employed in the ophthalmic compositions of the present invention is generally about 0.01 to 2.0% (w/v), preferably about 0.1% to 0.5% (w/v).

The amount of cyclodextrin to be employed in the ophthalmic compositions of the present invention is generally about 0.5 to 40% (w/v), preferably about 1.0% to 15% (w/v).

The ophthalmic compositions of the present invention are prepared by adding a cyclodextrin to an aqueous solution comprising the compound represented by Formula (I) so as to form an inclusion complex with the cyclodextrin. As a result, the aqueous solubility of the compound can be increased to a level sufficient for topical intraocular administration, which is undoubtedly desirable for long-term therapy of intraocular hypertension.

In the present invention, the compounds represented by Formula (I) are topically delivered non-systemically to the site of action, enhancing the effect, and minimizing entry into the central nervous system.

According to the present invention, after topical administration of, e.g., eyedrops, containing a compound represented by Formula (I) and a cyclodextrin, the compound is first released from the inclusion complex on the precorneal area where it is then able to penetrate across the cornea to reach the inner eye and the site of action.

It is commonly known that ophthalmic drugs decrease IOP less in normotensive rabbits than in hypertensive (glaucoma) rabbits (Vartiainen et al, *Invest. Ophthalmol. Vis. Sci.*, 33: 2019–2023 (1992); and Muchtar et al, *Ophthalmic. Res.*, 24: 142–149 (1992)). Generally, the rabbit is the most commonly used animal model in ocular drug research because its eye size is similar to humans, and it is relatively small and easy to handle (Greaves et al, *STP Pharm. Sci.*, 2: 13–33 (1992)).

It was found in the present invention that topical administration of 2-hydroxypropyl-β-cyclodextrin or heptakis-(2,6-di-O-methyl)-β-cyclodextrin in combination with the compound represented by Formula (I) are particularly effective in decreasing IOP in treated eyes of normotensive rabbits.

One aspect of the present invention is based on the discovery that unilateral application of the compounds represented by Formula (I) decreases the IOP in treated eyes, but does not greatly affect the IOP in untreated eyes in normotensive rabbits. Thus, it has been found for the first time in the present invention that these compounds act locally within the eye, perhaps via a specific receptor, rather than via a systemic (e.g., central nervous system) effect, and result in reduction of intraocular pressure.

The ophthalmic compositions of the present invention may also include water-soluble polymeric compounds for use as a viscosity enhancing agent. Examples of such water-soluble polymeric compounds include hydroxypropylmethyl cellulose, hydroxyethyl cellulose, hydroxypropyl cellulose, methyl cellulose, polyvinyl alcohols, sodium polyacrylate, sodium carboxymethyl cellulose, polyvinyl pyrrolidone, hyaluronic acid and polyacrylic acid.

The viscosity enhancing agents may be used in the ophthalmic compositions of the present invention in amounts which result in a viscosity in the range of about 1 to 1,000 cP, preferably about 5 to 50 cP.

The ophthalmic compositions of the present invention may further comprise a buffering agent, such as acetate, citrate, phosphate and borate buffers, or mixtures of these buffers.

The concentration of the buffering agent which may be used in the ophthalmic compositions of the present invention is in the range of about 1.0 mM to 200 mM, preferably about 10 mM to 100 mM.

The pH of the ophthalmic composition of the present invention should be in the range of about 4.0 to 8.0, and more specifically about 6.0 to 7.4.

The ophthalmic compositions of the present invention may also include additional carrier adjuvants, including conventional additives, such as a preservative (e.g., benzalkonium chloride, benzyl alcohol, chlorbutanol, chlorhexidine, etc.) or an antioxidant (e.g., sodium bisulfite, sodium thiosulfite, EDTA, etc.). The concentration of these additives in the composition will be selected according to their type/concentration.

The pharmaceutically effective amount of the compound represented by Formula (I) to be topically administered to the effected eye will generally vary depending upon the age, weight, sex and severity of hypertension in the eye. Typically, the pharmaceutically effective amount will be in the range of about 0.05 to 30 µg/kg body weight, preferably about 0.5 to 10 µg/kg body weight.

The following examples are provided for illustrative purposes only, and are in no way intended to limit the scope of the present invention.

EXAMPLE 1

In this example, the effect of a 0.125% (w/v) arachidonylethanolamide solution on intraocular pressure (IOP) of normotensive pigmented rabbits weighing between 2.1–3.6 kg (n=6) was studied. The rabbits were housed separately in cages under standard laboratory conditions, i.e., 10 hr dark/14 hr light cycle.

More specifically, 6.25 mg of arachidonylethanolamide and 250 mg of 2-OH-propyl-$\beta$-CD were added to 5.0 ml of distilled water, and the solution was adjusted to pH 7.0 with sodium hydroxide/hydrochloric acid. Then, distilled water was added to adjust the total volume to 5.0 ml. The osmolality of the solution was adjusted to isotonic, 316 mOsm/kg, with sodium chloride.

As a control, a 0.9% (w/v) NaCl was also prepared.

Then, 25 µl of either the drug-CD solution or the NaCl solution was administered unilaterally to the rabbits. The rabbits were kept in restraint boxes during the study.

IOP was measured using a BioRad (Cambridge, Mass.) Digilab Modular One Pneumatonometer. Before each measurement, one or two drops of 0.06% (w/v) oxybuprocaine were applied to the cornea as an anaesthetic before tonometry to eliminate discomfort. For each determination, at least two readings were taken from each eye. The measurements were started 2 hr before drug-CD or 0.9% (w/v) NaCl solution administration, and were continued for 5 hr after administration.

The IOPs of the pigmented rabbits at the time of eyedrop administration were between 18.8–24.9 mmHg (n=6).

Figure 1B:
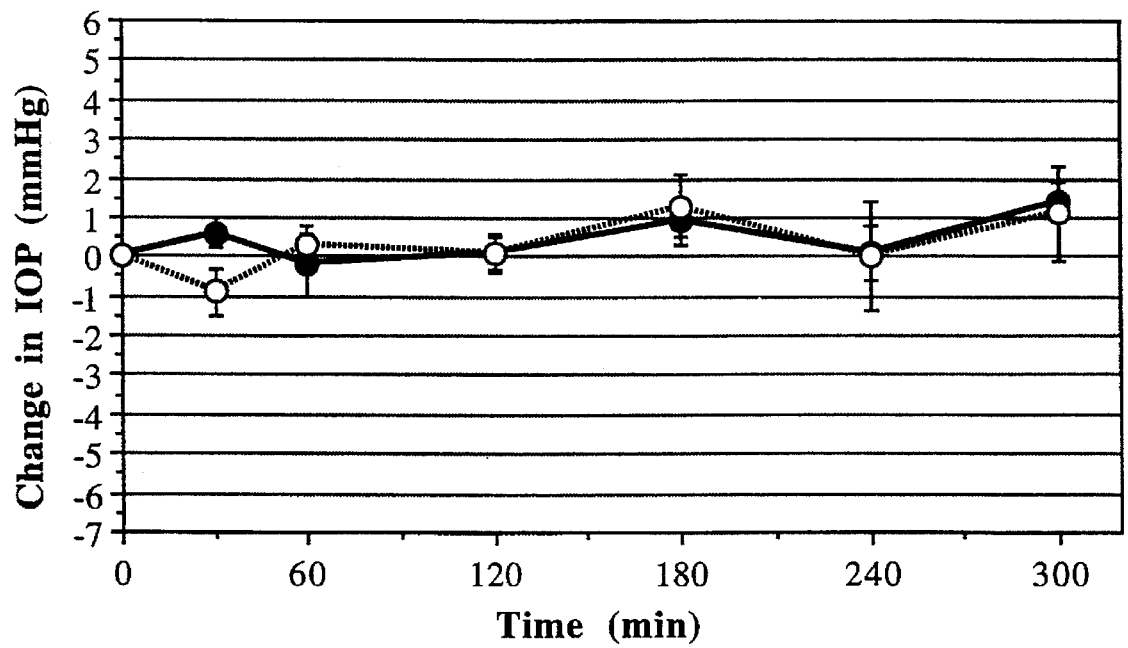
FIG. 1B shows the IOP changes in normotensive pigmented rabbits (untreated eyes) after unilateral ocular administration (25 μl) of 0.125% (w/v) arachidonylethanolamide (o) or 0.9% (w/v) NaCl (●), mean ± S.E. (n=6).

The results are shown in FIG. 1A and 1B, and Table I below. All of the values are expressed as the mean ± standard error of means (X ± S.E.).

TABLE I

Intraocular Pressure Changes (mmhg) at Predetermined Times (h) in Normotensive Pigmented Rabbits After Unilateral Administration of Eyedrops (mean ± S.E., n = 5–6)

| Solution | 0 h | 0.5 h | 1 h | 2 h | 3 h | 4 h | 5 h |
|---|---|---|---|---|---|---|---|
| Treated eye | | | | | | | |
| 0.125% Arachidonylethanolamide in 5.0% 2-OH-propyl-$\beta$-CD | 0 ± 0 | −1.5 ± 1.4 | −3.5 ± 0.5 | −2.6 ± 0.8 | −0.5 ± 0.8 | −1.6 ± 1.1 | −0.3 ± 1.2 |
| 0.25% Arachidonylethanolamide in 5.0% 2-OH-propyl-$\beta$-CD | 0 ± 0 | 2.5 ± 1.3 | −3.4 ± 1.0 | −5.2 ± 1.3 | −2.6 ± 1.6 | −0.9 ± 1.5 | −0.2 ± 3.1 |
| 0.9% NaCl | 0 ± 0 | 0.8 ± 0.7 | −1.0 ± 0.8 | −0.1 ± 0.6 | 0.6 ± 0.5 | −0.2 ± 0.8 | 1.5 ± 0.8 |
| 5.0% 2-OH-propyl-$\beta$-CD | 0 ± 0 | 0.4 ± 0.8 | 0.2 ± 1.2 | 0.4 ± 0.5 | 0.2 ± 0.7 | 1.4 ± 1.7 | 1.5 ± 1.3 |
| 12.5% 2-OH-propyl-$\beta$-CD | 0 ± 0 | 0.0 ± 1.1 | −0.1 ± 1.3 | −0.7 ± 1.1 | 0.2 ± 0.8 | 0.8 ± 0.9 | 2.1 ± 0.9 |
| 0.25% Arachidonylethanolamide in 2.5% heptakis-(2,6-di-O-methyl) $\beta$-CD | 0 ± 0 | 1.5 ± 0.8 | −1.3 ± 0.5 | −3.1 ± 0.8 | −2.2 ± 1.6 | −0.9 ± 0.5 | −1.5 ± 1.1 |

TABLE I-continued

Intraocular Pressure Changes (mmhg) at Predetermined
Times (h) in Normotensive Pigmented Rabbits After Unilateral
Administration of Eyedrops (mean ± S.E., n = 5–6)

| Solution | 0 h | 0.5 h | 1 h | 2 h | 3 h | 4 h | 5 h |
|---|---|---|---|---|---|---|---|
| Untreated eye (contralateral) | | | | | | | |
| 0.125% Arachidonylethanolamide in 5.0% 2-OH-propyl-β-CD | 0 ± 0 | −0.9 ± 0.6 | 0.3 ± 0.5 | 0.1 ± 0.4 | 1.3 ± 0.8 | 0.0 ± 1.4 | 1.1 ± 0.2 |
| 0.25% Arachidonylethanolamide in 5.0% 2-OH-propyl-β-CD | 0 ± 0 | −2.1 ± 0.3 | −1.6 ± 1.1 | −0.3 ± 1.7 | −0.3 ± 1.5 | 0.3 ± 1.8 | −0.1 ± 1.5 |
| 0.9% NaCl | 0 ± 0 | 0.6 ± 0.4 | −0.2 ± 0.8 | 0.1 ± 0.5 | 0.9 ± 0.6 | 0.1 ± 0.7 | 1.4 ± 0.5 |
| 5.0% 2-OH-propyl-β-CD | 0 ± 0 | −1.4 ± 0.3 | −1.3 ± 0.9 | −0.4 ± 0.6 | −1.5 ± 1.6 | 0.4 ± 0.8 | 0.9 ± 0.7 |
| 12.5% 2-OH-propyl-β-CD | 0 ± 0 | −0.6 ± 1.2 | −1.1 ± 0.7 | −1.4 ± 1.0 | 0.6 ± 1.4 | 0.8 ± 1.2 | 0.5 ± 1.2 |
| 0.25% Arachidonylethanolamide in 2.5% heptakis-(2,6-di-O-methyl) β-CD | 0 ± 0 | 1.0 ± 0.4 | −0.4 ± 0.6 | 0.2 ± 0.5 | 0.5 ± 0.6 | 1.8 ± 0.6 | 0.9 ± 0.7 |

As shown in FIG. 1A and Table I above, unilateral intraocular administration of arachidonylethanolamide decreases the IOP in treated eyes in normotensive pigmented rabbits when compared to administration of a 0.9% (w/v) NaCl solution. In the treated eyes of normotensive pigmented rabbits, cyclodextrin vehiculated arachidonylethanolamide showed a maximal IOP reduction of 3.5 mmHg, 1 hr after 0.125% (w/v) arachidonylethanolamide treatment.

However, as shown in FIG. 1B and Table I above, unilateral intraocular administration of arachidonylethanolamide does not greatly affect the IOP in the contralateral (untreated) eye in normotensive pigmented rabbits when compared to administration of the 0.9% (w/v) NaCl solution. In the contralateral eye of normotensive pigmented rabbits, the maximal IOP reduction was 0.9 mmHg, 30 min after 0.125% (w/v) arachidonylethanolamide treatment.

EXAMPLE 2

In this example, the effect of a 0.25% (w/v) arachidonylethanolamide solution on intraocular pressure (IOP) of normotensive pigmented (weighing between 2.1–3.6 kg, n=6) and albino (New Zealand strain) rabbits (weighing between 3.3–4.3 kg (n=4)) of both sexes was studied. The rabbits were housed separately in cages under standard laboratory conditions, i.e., 10 hr dark/14 hr light cycle.

More specifically, 12.5 mg of arachidonylethanolamide and 250 mg of 2-OH-propyl-β-CD were added to 5.0 ml of distilled water, and the solution was adjusted to pH 7.0 with sodium hydroxide/hydrochloric acid. Then, distilled water was added to adjust the total volume to 5.0 ml. The osmolality of the solution was adjusted to isotonic, 301 mOsm/kg, with sodium chloride.

As a control, a 0.9% (w/v) NaCl was also prepared.

Then, 25 μl of the drug-CD solution or the NaCl solution was administered unilaterally. Again, the rabbits were kept in restraint boxes during the study, and IOP was measured using a BioRad (Cambridge, Mass.) Digilab Modular One Pneumatonometer. Also, before each measurement, one or two drops of 0.06% (w/v) oxybuprocaine were applied to the cornea before tonometry to eliminate discomfort. For each determination at least two readings were taken from each eye. The measurements were started 2 hr before drug-CD or 0.9% (w/v) NaCl solution administration, and were continued 5 hr after administration.

The IOPs of pigmented and albino rabbits at the time of eyedrop administration were between 19.6–27.2 mmHg (n=6) and 12.4–23.8 mmHg (n=4), respectively.

The results are shown in FIG. 2A and 2B, FIGS. 3A and 3B, and Table I above and Table II below. All of the values are expressed as the mean ± standard error of means (X ± S.E.).

TABLE II

Intraocular Pressure Changes (mmhg) at Predetermined Times (h) in Normotensive Albino Rabbits After Unilateral Administration of Eyedrops (mean ± S.E., n = 4)

| Solution | 0 h | 0.5 h | 1 h | 2 h | 3 h | 4 h | 5 h |
|---|---|---|---|---|---|---|---|
| Treated eye | | | | | | | |
| 0.25% Arachidonyl-ethanolamide in 5.0% 2-OH-propyl-β-CD | 0 ± 0 | 2.1 ± 0.9 | −1.3 ± 2.5 | −4.4 ± 1.7 | −2.5 ± 1.2 | −0.5 ± 1.1 | −0.6 ± 0.9 |
| 0.9% NaCl | 0 ± 0 | −0.9 ± 0.8 | −0.3 ± 0.7 | 0.8 ± 1.0 | −0.4 ± 0.4 | 0.8 ± 0.4 | 0.9 ± 0.9 |
| 30% 2-OH-propyl-β-CD | 0 ± 0 | 0.4 ± 0.8 | −0.5 ± 1.3 | 1.2 ± 0.9 | 0.5 ± 1.2 | 0.7 ± 1.5 | 1.7 ± 1.5 |
| Untreated eye (contralateral) | | | | | | | |
| 0.25% Arachidonyl-ethanolamide in 5.0% 2-OH-propyl-β-CD | 0 ± 0 | −1.1 ± 0.7 | −1.2 ± 0.6 | 0.4 ± 0.7 | 0.7 ± 0.8 | 0.8 ± 1.4 | 0.8 ± 0.5 |
| 0.9% NaCl | 0 ± 0 | −1.2 ± 0.4 | −1.7 ± 0.4 | 0.0 ± 0.7 | −0.3 ± 0.6 | 1.1 ± 0.7 | 1.7 ± 0.8 |
| 30% 2-OH-propyl-β-CD | 0 ± 0 | −0.1 ± 0.5 | −1.3 ± 0.6 | −0.5 ± 1.1 | −0.9 ± 0.4 | 0.2 ± 1.0 | −0.1 ± 0.7 |

Figure 2A:
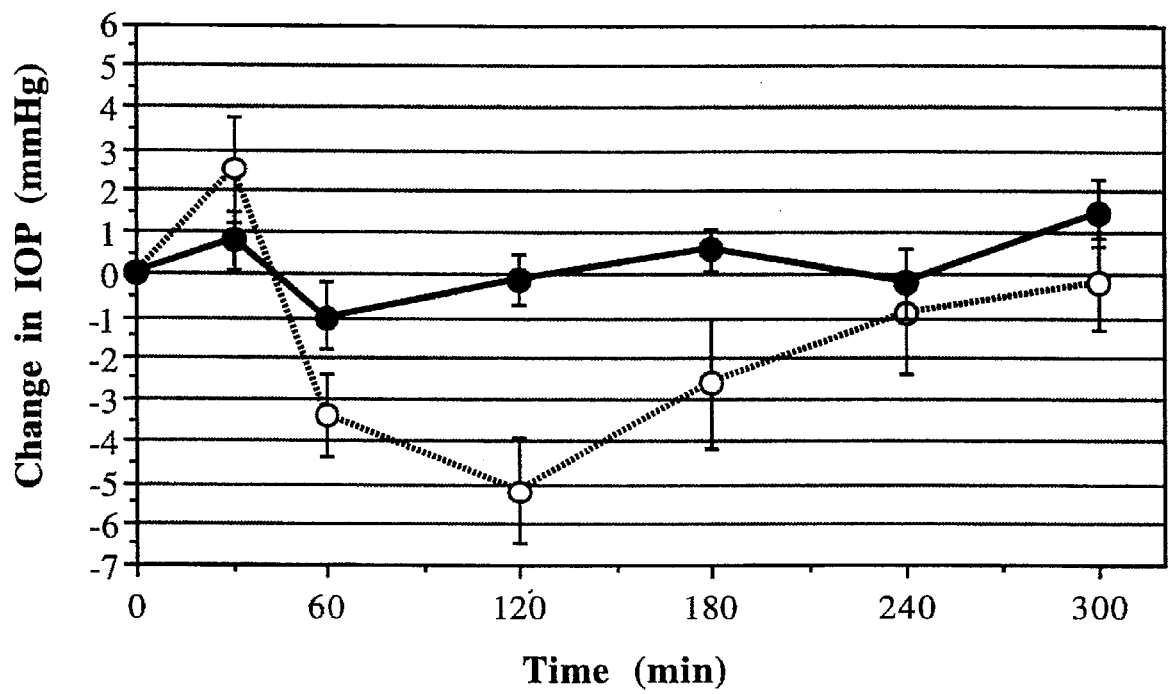
FIG. 2A shows the IOP changes in normotensive pigmented rabbits (treated eyes) after unilateral ocular administration (25 μl) of 0.25% (w/v) arachidonylethanolamide (o) or 0.9% (w/v) NaCl (●), mean ± S.E. (n=6).

As shown in FIG. 2A and Table I above, unilateral intraocular administration of arachidonylethanolamide decreases the IOP in treated eyes in normotensive pigmented rabbits when compared to administration of the 0.9% (w/v) NaCl solution. In the treated eyes of normotensive pigmented rabbits, cyclodextrin vehiculated arachidonylethanolamide showed a maximal IOP reduction of 5.2 mmHg, 2 hr after 0.25% (w/v) arachidonylethanolamide treatment.

Figure 2B:
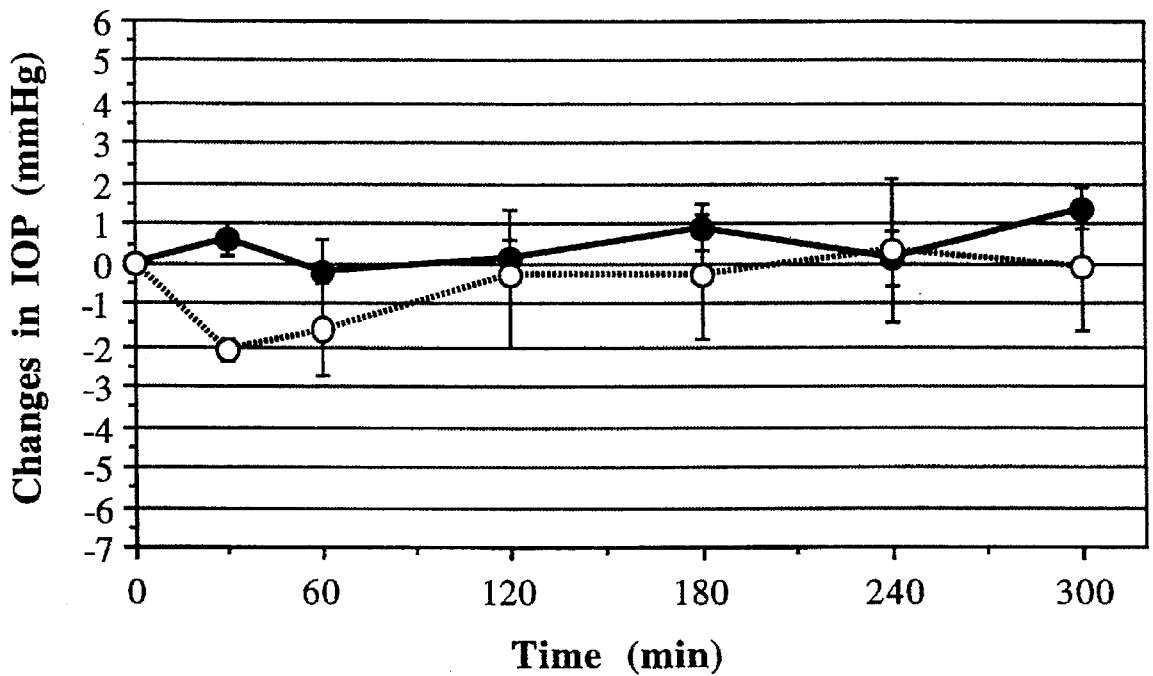
FIG. 2B shows the IOP changes in normotensive pigmented rabbits (untreated eyes) after unilateral ocular administration (25 μl) of 0.25% (w/v) arachidonylethanolamide (o) or 0.9% (w/v) NaCl (●), mean ± S.E. (n=6).

On the other hand, as shown in FIG. 2B and Table I above, unilateral intraocular administration of arachidonylethanolamide does not greatly affect the IOP in the contralateral (untreated) eye in normotensive pigmented rabbits when compared to administration of the 0.9% (w/v) NaCl solution. Specifically, in the contralateral eye of normotensive pigmented rabbits, the maximal IOP reduction was 2.1 mmHg, 30 min after 0.25% (w/v) arachidonylethanolamide treatment.

Figure 3A:
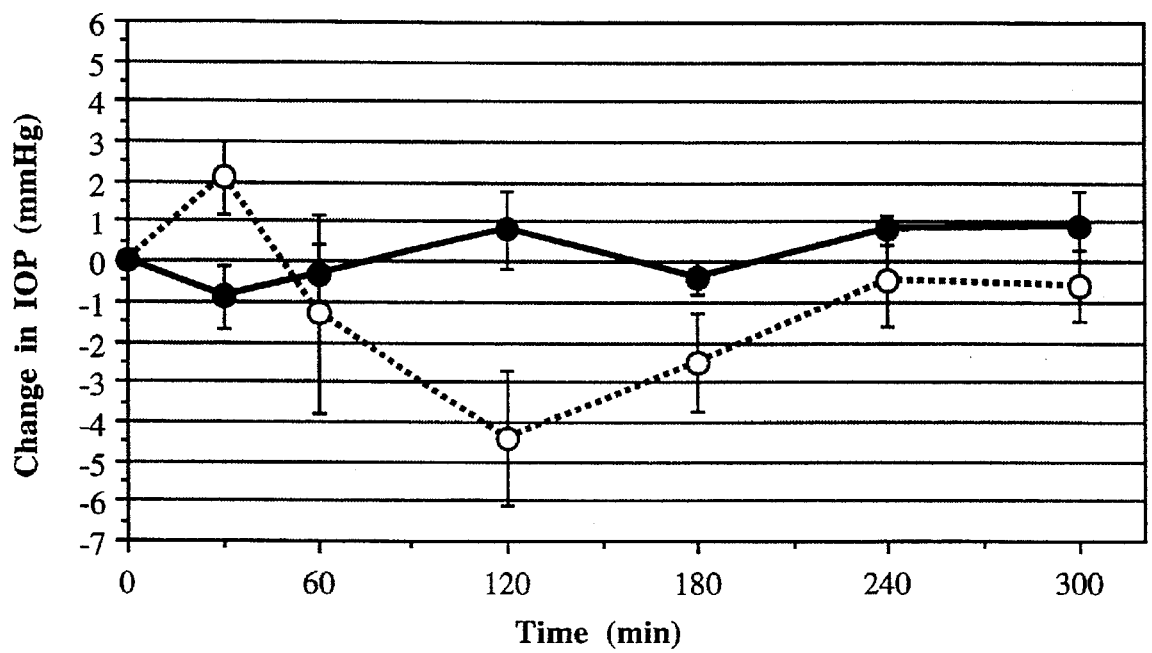
FIG. 3A shows the IOP changes in normotensive albino rabbits (treated eyes) after unilateral ocular administration (25 μl) of 0.25% (w/v) arachidonylethanolamide (o) or 0.9% (w/v) NaCl (●), means ± S.E. (n=4).

Similarly, as shown in FIG. 3A and Table II above, unilateral intraocular administration of arachidonylethanolamide also decreases the IOP in treated eyes in normotensive albino rabbits when compared to administration of the 0.9% (w/v) NaCl solution. Specifically, in the treated eyes of normotensive albino rabbits, cyclodextrin vehiculated arachidonylethanolamide showed a maximal IOP reduction of 4.4 mmHg, 2 hr after 0.25% (w/v) arachidonylethanolamide treatment.

Figure 3B:
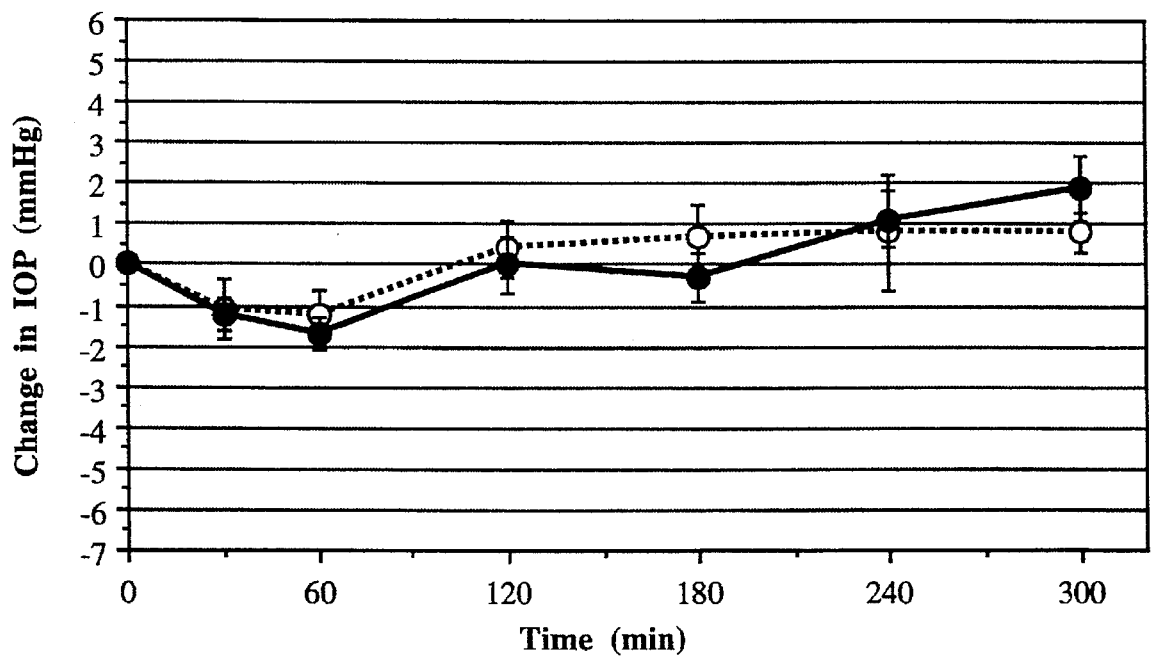
FIG. 3B shows the IOP changes in normotensive albino rabbits (untreated eyes) after unilateral ocular administration (25 μl) of 0.25% (w/v) arachidonylethanolamide (o) or 0.9% (w/v) NaCl (●) means ± S.E. (n=4).

However, as shown in FIG. 3B and Table II above, no great affect on the IOP in the contralateral (untreated) eye in normotensive albino rabbits was seen when compared to administration of the 0.9% (w/v) NaCl solution. In particular, in the contralateral eye of normotensive pigmented rabbits, the maximal IOP reduction was 1.3 mmHg, 60 min after 0.25% (w/v) arachidonylethanolamide treatment.

EXAMPLE 3

In this example, the effect of a 12.5% (w/v) 2-OH-propyl-β-cyclodextrin solution on intraocular pressure (IOP) of normotensive pigmented rabbits (weighing between 2.1–3.6 kg; n=6) of both sexes was studied. The rabbits were housed separately in cages under standard laboratory conditions, i.e., 10 hr dark/14 hr light cycle.

More specifically, 1250 mg of 2-OH-propyl-β-CD was added to 10.0 ml of distilled water, and the solution was adjusted to pH 5.0 with sodium hydroxide/hydrochloric acid. Then, distilled water was added to adjust the total volume to 10 ml. The osmolality of the solution was adjusted to isotonic, 300 mOsm/kg, with sodium chloride.

As a control, a 0.9% (w/v) NaCl was also prepared.

Then, 25 μl of the 12.5% (w/v) CD solution or the NaCl solution was administered unilaterally. Again, the rabbits were kept in restraint boxes during the study and IOP was measured using a BioRad (Cambridge, Mass.) Digilab Modular One Pneumatonometer. Before each measurement, one or two drops of 0.06% (w/v) oxybuprocaine were applied to the cornea before tonometry to eliminate discomfort. For each determination at least two readings were taken from each eye. The measurements were started 2 hr before CD or 0.9% (w/v) NaCl solution administration, and were continued 5 hr after administration.

The IOPs of the pigmented rabbits at the time of eyedrop administration were between 18.9–25.7 mmHg (n=6).

Figure 4A:
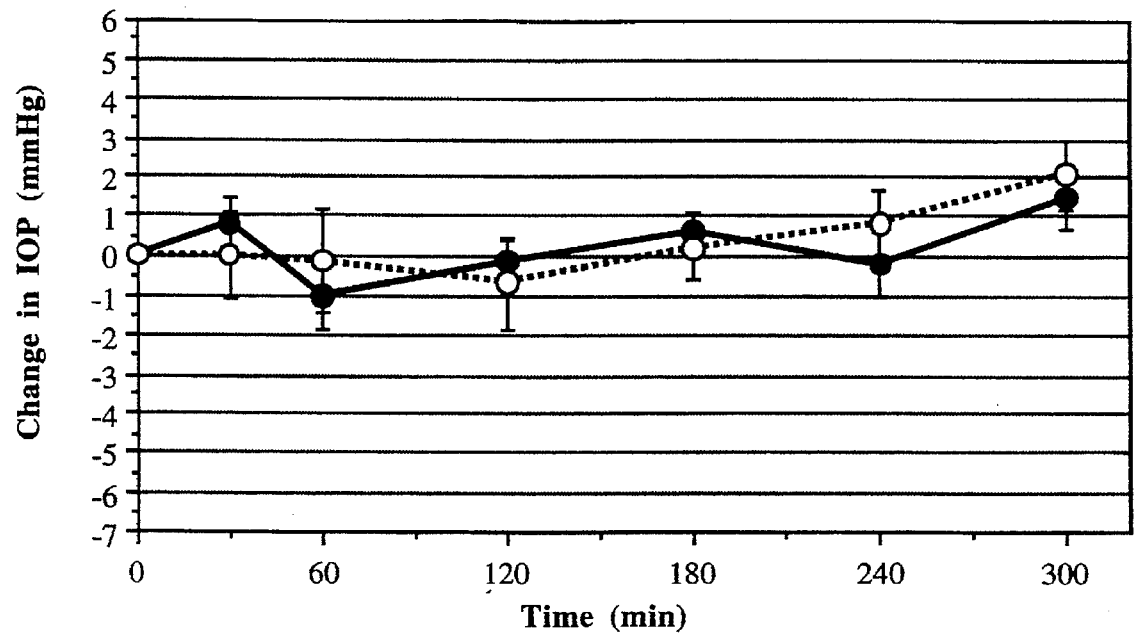
FIG. 4A shows the IOP changes in normotensive pigmented rabbits (treated eyes) after unilateral ocular administration (25 μl) of 12.5% (w/v) 2-OH-propyl-β-cyclodextrin (o) or 0.9% (w/v) NaCl (●), mean ± S.E. (n=6).
Figure 4B:
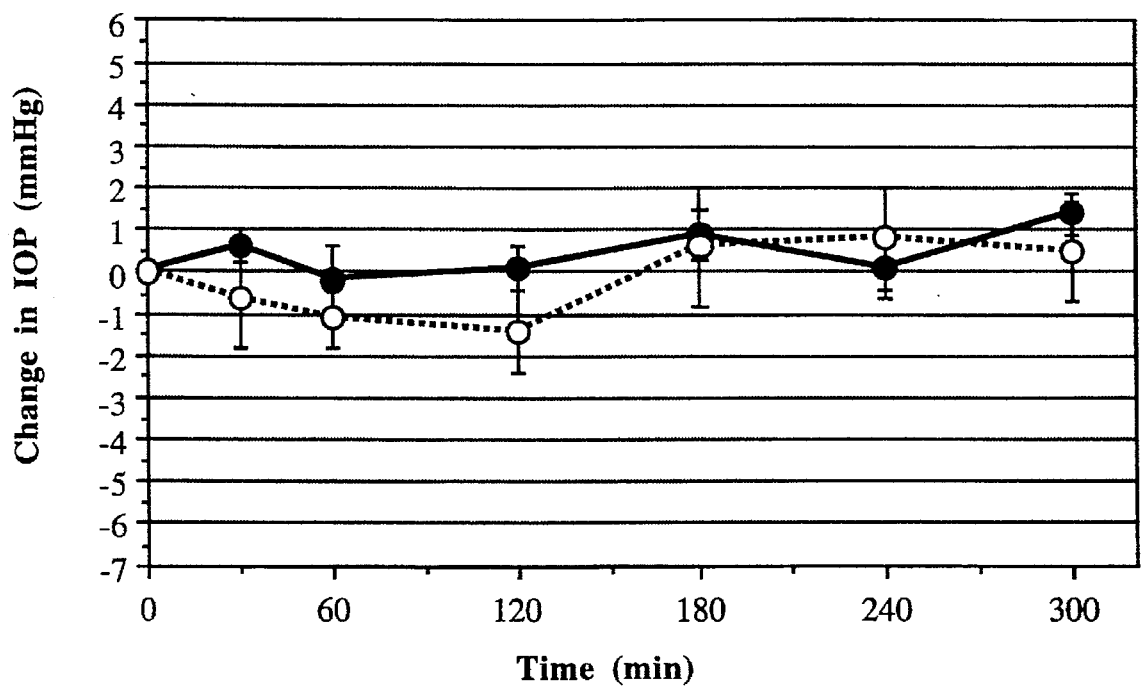
FIG. 4B shows the IOP changes in normotensive pigmented rabbits (untreated eyes) after unilateral ocular administration (25 μl) of 12.5% (w/v) 2-OH-propyl-β-cyclodextrin (o) or 0.9% (w/v) NaCl (●), mean ± S.E. (n=6).

The results are shown in FIGS. 4A and 4B, and Table I above. All of the values are expressed as the mean ± standard error of means (X ± S.E.).

As shown in FIGS. 4A and 4B, and Table I above, the unilateral intraocular administration of a 12.5% (w/v) solution of 2-OH-propyl-β-cyclodextrin alone does not greatly affect the IOP of treated or untreated (contralateral) eyes in normotensive pigmented rabbits when compared to administration of the 0.9% (w/v) NaCl solution.

EXAMPLE 4

In this example, the effect of a 30% (w/v) 2-OH-propyl-β-cyclodextrin solution on intraocular pressure (IOP) of normotensive albino (New Zealand strain) rabbits (weighing between 3.3–4.3 kg, n=4) of both sexes was studied. The rabbits were housed separately in cages under standard laboratory conditions, i.e., 10 hr dark/14 hr light cycle.

More specifically, 3000 mg of 2-OH-propyl-β-CD were added to 10 ml of distilled water, and the solution was adjusted to pH 7.0 with sodium hydroxide/hydrochloric acid. Then, distilled water was added to adjust the total volume to 10 ml. The osmolality of the solution was adjusted to isotonic, 436 mOsm/kg, with sodium chloride.

As a control, a 0.9% (w/v) NaCl was also prepared.

Then, 25 µl of the 30% (w/v) CD solution or the NaCl solution was administered unilaterally. The rabbits were kept in restraint boxes during the study, and IOP was measured using a BioRad (Cambridge, Mass.) Digilab Modular One Pneumatonometer. Before each measurement, one or two drops of 0.06% (w/v) oxybuprocaine were applied to the cornea before tonometry to eliminate discomfort. For each determination at least two readings were taken from each eye. The measurements were started 2 hr before the CD or 0.9% (w/v) NaCl solution administration, and were continued 5 hr after administration.

The IOPs of the albino rabbits at the time of eyedrop administration were between 12.4–23.8 mmHg (n=4).

Figure 5A:
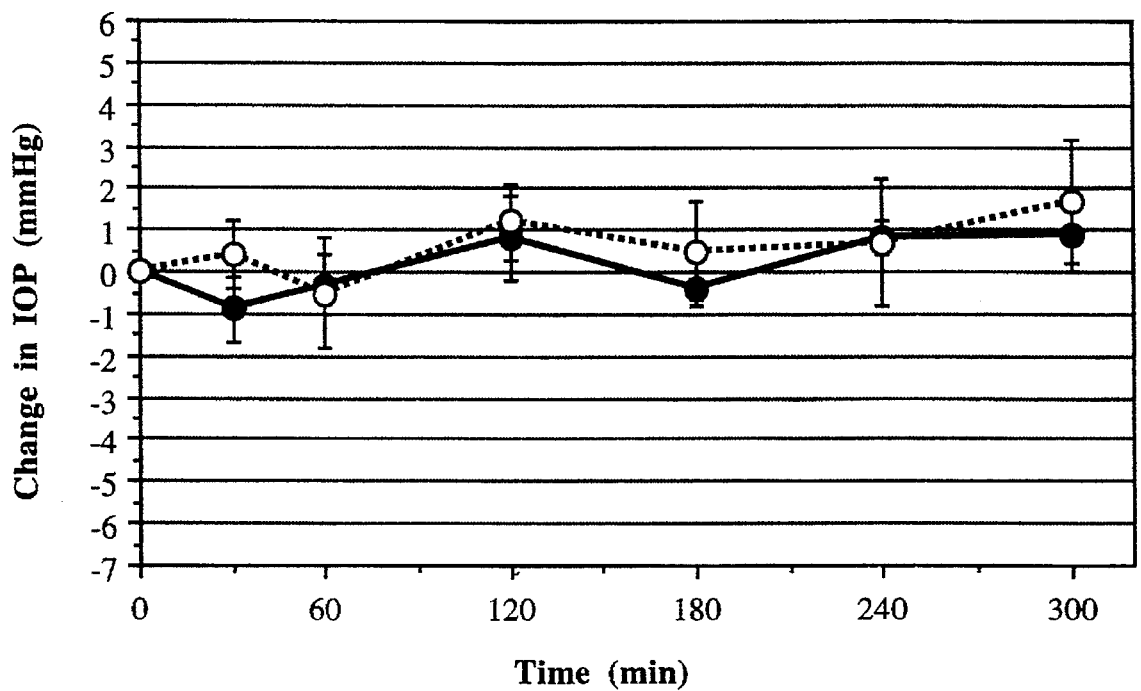
FIG. 5A shows the IOP changes in normotensive albino rabbits (treated eyes) after unilateral ocular administration (25 μl) of 30% (w/v) 2-OH-propyl-β-cyclodextrin (o) or 0.9% (w/v) NaCl (●), mean ± S.E. (n=4).
Figure 5B:
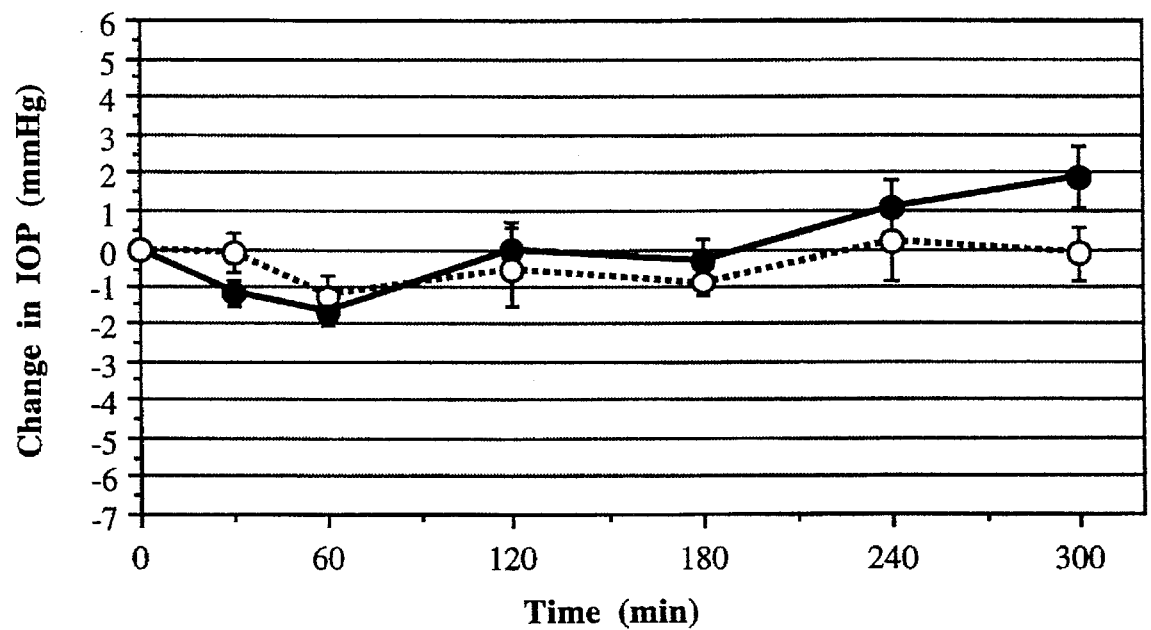
FIG. 5B shows the IOP changes in normotensive albino rabbits (untreated eyes) after unilateral ocular administration (25 μl) of 30% (w/v) 2-OH-propyl-β-cyclodextrin (o) or 0.9% (w/v) NaCl (●), mean ± S.E. (n=4).

The results are shown in FIGS. 5A and 5B, and Table II above. All of the values are expressed as the mean ± standard error of means (X ± S.E.).

As shown in FIGS. 5A and 5B, and Table II above, the unilateral intraocular administration of a 30% (w/v) solution of 2-OH-propyl-β-cyclodextrin alone does not greatly affect the IOP of treated or untreated (contralateral) eyes in normotensive albino rabbits when compared to administration of the 0.9% (w/v) NaCl solution.

EXAMPLE 5

In this example, the effect of a 5.0% (w/v) 2-OH-propyl-β-cyclodextrin solution on intraocular pressure (IOP) of normotensive pigmented rabbits (weighing between 2.6–3.6 kg; n=5) of both sexes was studied. The rabbits were housed separately in cages under standard laboratory conditions, i.e., 10 hr dark/14 hr light cycle.

More specifically, 250 mg of 2-OH-propyl-β-CD was added to 5.0 ml of distilled water, and the solution was adjusted to pH 7.0 with sodium hydroxide/hydrochloric acid. Then, distilled water was added to adjust the total volume to 5.0 ml. The osmolality of the solution was adjusted to isotonic, 301 mOsm/kg, with sodium chloride.

As a control, a 0.9% (w/v) NaCl was also prepared.

Then, 25 µl of the 5.0% (w/v) CD solution or the NaCl solution was administered unilaterally. Again, the rabbits were kept in restraint boxes during the study and IOP was measured using a BioRad (Cambridge, Mass.) Digilab Modular One Pneumatonometer. Before each measurement, one or two drops of 0.06% (w/v) oxybuprocaine were applied to the cornea before tonometry to eliminate discomfort. For each determination at least two readings were taken from each eye. The measurements were started 2 hr before CD or 0.9% (w/v) NaCl solution administration, and were continued 5 hr after administration.

The IOPs of the pigmented rabbits at the time of eyedrop administration were between 15.2–21.9 mmHg (n=5).

Figure 6A:
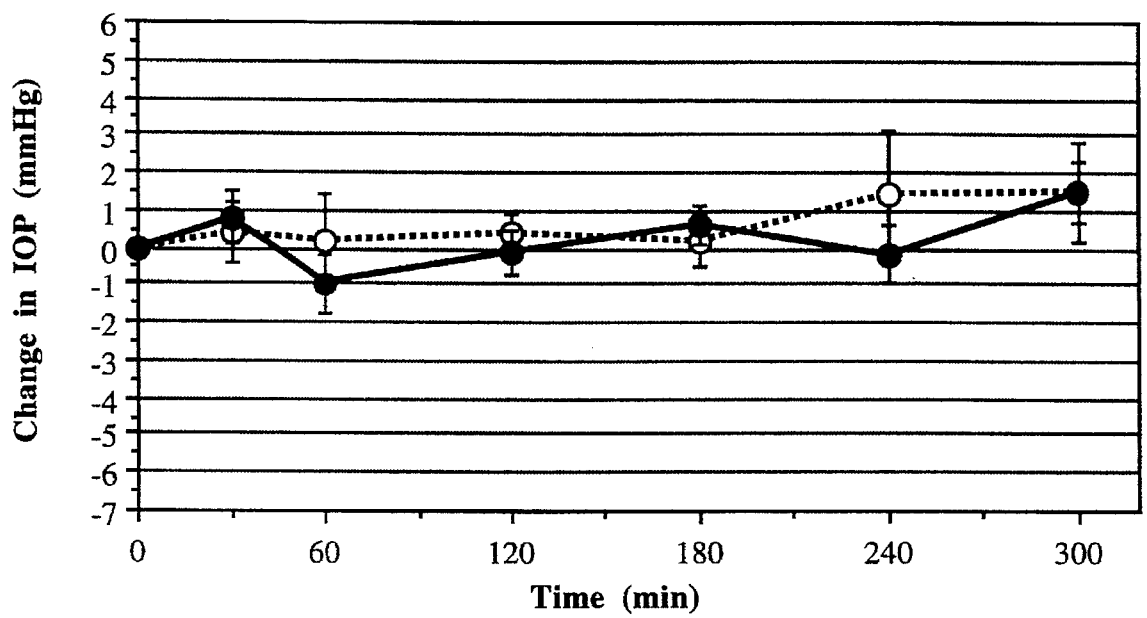
FIG. 6A shows the IOP changes in normotensive pigmented rabbits (treated eyes) after unilateral ocular administration (25 μl) of 5% (w/v) 2-OH-propyl-β-cyclodextrin (o) or 0.9% (w/v) NaCl (●), mean ± S.E. (n=5).
Figure 6B:
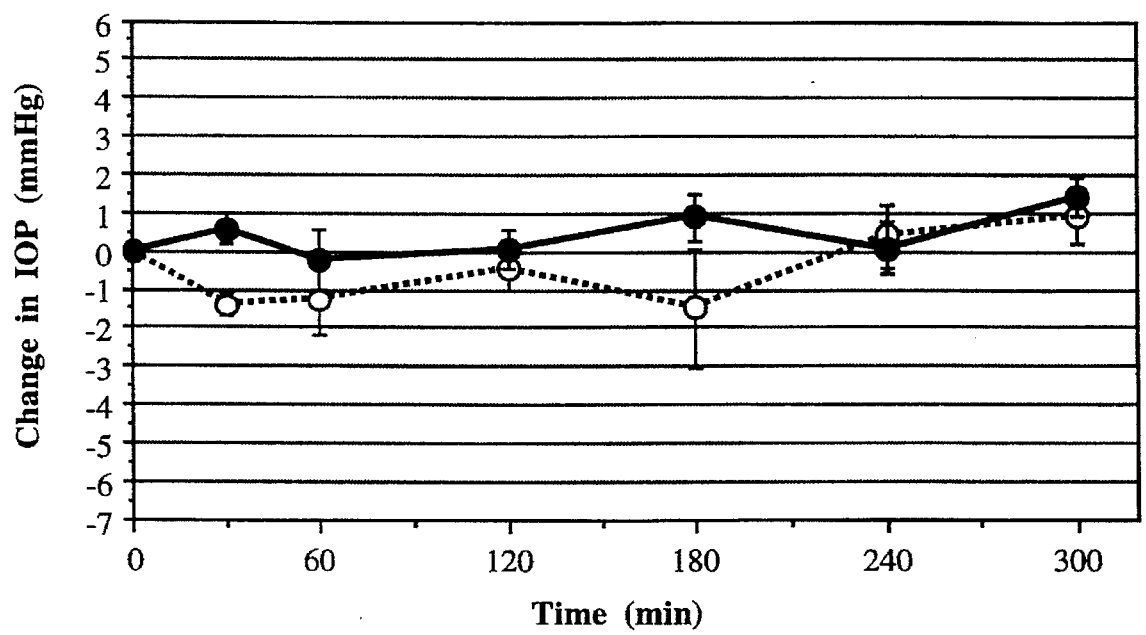
FIG. 6B shows the IOP changes in normotensive pigmented rabbits (untreated eyes) after unilateral ocular administration (25 μl) of 5% (w/v) 2-OH-propyl-β-cyclodextrin (o) or 0.9% (w/v) NaCl (●), mean ± S.E. (n=5).

The results are shown in FIGS. 6A and 6B, and Table I above. All of the values are expressed as the mean ± standard error of means (X ± S.E.).

As shown in FIGS. 6A and 6B, and Table I above, the unilateral intraocular administration of a 5.0% (w/v) solution of 2-OH-propyl-β-cyclodextrin alone does not greatly affect the IOP of treated or untreated (contralateral) eyes in normotensive pigmented rabbits when compared to administration of the 0.9% (w/v) NaCl solution.

EXAMPLE 6

In this example, the effect of a 0.25% (w/v) arachidonyl-propanolamide solution on IOP of normotensive pigmented rabbits weighing between 2.6–3.6 kg (n=6) was studied. The rabbits were housed separately in cages under standard laboratory conditions, i.e., 10 hr dark/14 hr light cycle.

More specifically, 12.5 mg of arachidonylpropanolamide and 375 mg of 2-OH-propyl-β-CD were added to distilled water, and the solution was adjusted to pH 7.0 with sodium hydroxide/hydrochloric acid. Then, distilled water was added to adjust the total volume to 5.0 ml. The osmolality of the solution was adjusted to isotonic, 298 mOsm/kg, with sodium chloride.

As a control, a 0.9% (w/v) NaCl was also prepared.

Then, 25 µl of either the drug-CD solution or the NaCl solution was administered unilaterally to the rabbits. The rabbits were kept in restraint boxes during the study.

IOP was measured using a BioRad (Cambridge, Mass.) Digilab Modular One Pneumatonometer. Before each measurement, one or two drops of 0.06% (w/v) oxybuprocaine were applied to the cornea as an anaesthetic before tonometry to eliminate discomfort. For each determination, at least two readings were taken from each eye. The measurements were started 2 hr before drug-CD or 0.9% (w/v) NaCl solution administration, and were continued for 5 hr after administration.

The IOPs of the pigmented rabbits at the time of eyedrop administration were between 14.0–29.7 mmHg (n=6).

Figure 7A:
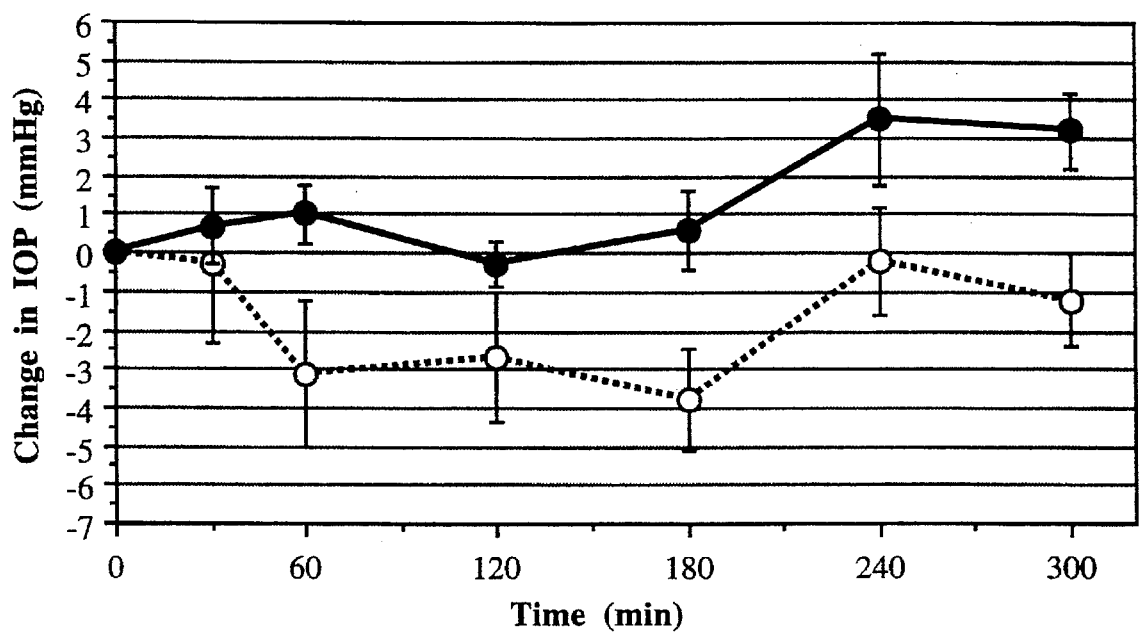
FIG. 7A shows the IOP changes in normotensive pigmented rabbits (treated eyes) after unilateral ocular administration (25 μl) of 0.25% (w/v) arachidonylpropanolamide (o) or 0.9% (w/v) NaCl (●) mean ± S.E. (n=6).
Figure 7B:
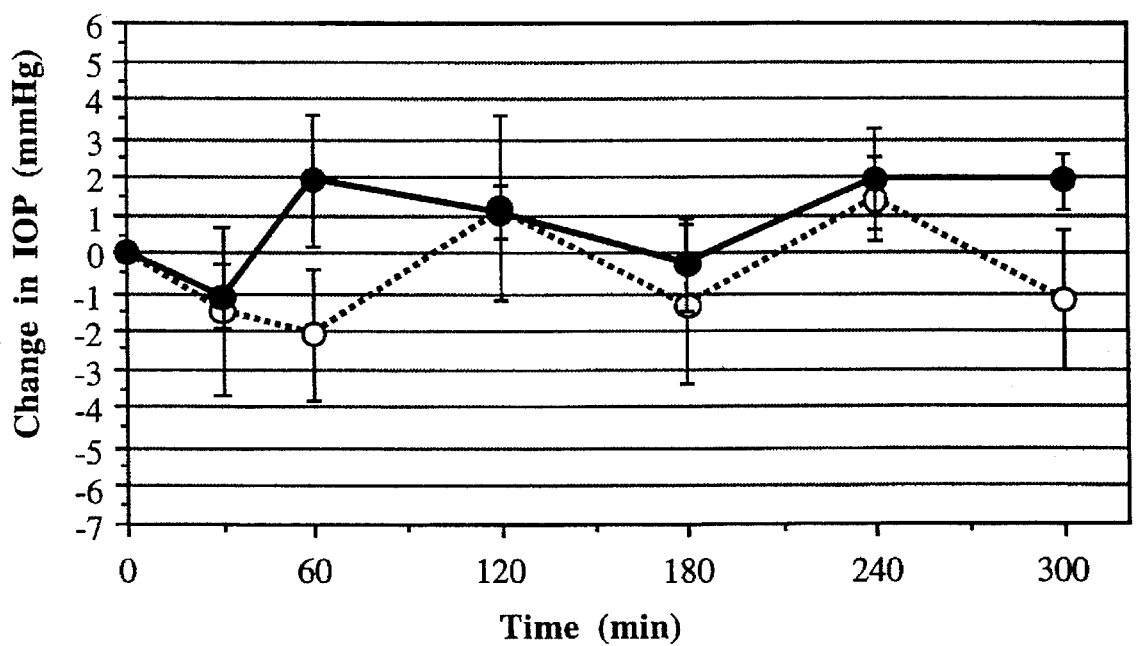
FIG. 7B shows the IOP changes in normotensive pigmented rabbits (untreated eyes) after unilateral ocular administration (25 μl) of 0.25% (w/v) arachidonylpropanolamide (o) or 0.9% (w/v) NaCl (●), mean ± S.E. (n=6).

The results are shown in FIGS. 7A and 7B, and Table III below. All of the values are expressed as the mean ± standard error of means (X ± S.E.).

TABLE III

Intraocular Pressure Changes (MmHg) at Predetermined Times (h) in Normotensive Pigmented Rabbits After Unilateral Administration of Eyedrops (mean ± S.E., n = 5–6)

| Solution | 0 h | 0.5 h | 1 h | 2 h | 3 h | 4 h | 5 h |
|---|---|---|---|---|---|---|---|
| *Treated eye* | | | | | | | |
| 0.9% NaCl | 0 ± 0 | 0.7 ± 1.0 | 1.0 ± 0.8 | −0.3 ± 0.6 | 0.6 ± 1.0 | 3.5 ± 1.7 | 3.2 ± 1.0 |
| 0.25% Arachidonyl-propanolamide in 7.5% 2-OH-propyl-β-CD | 0 ± 0 | −0.3 ± 2.0 | −3.1 ± 1.9 | −2.7 ± 1.7 | −3.8 ± 1.3 | −0.2 ± 1.4 | −3.2 ± 1.2 |
| 0.25% 8,11,14-Eicosatrienyl-ethanolamide in 7.5% 2-OH-propyl-β-CD | 0 ± 0 | −2.1 ± 0.8 | −1.6 ± 2.3 | −2.1 ± 1.5 | −2.5 ± 0.8 | 6.5 ± 1.9 | 0.5 ± 1.9 |
| 0.25% 7,10,13,16-Docosatetraenyl-ethanolamide in 7.5% 2-OH-propyl-β-CD | 0 ± 0 | 0.7 ± 1.3 | −1.2 ± 1.5 | −0.5 ± 1.5 | −2.7 ± 0.3 | −2.5 ± 0.8 | −0.5 ± 1.2 |
| 0.25% Arachidonyl-ethanethiolamide in 10% 2-OH-propyl-β-CD | 0 ± 0 | −0.6 ± 0.9 | −0.9 ± 1.0 | −2.3 ± 0.4 | 0.0 ± 0.0 | −2.2 ± 1.0 | −2.4 ± 0.5 |
| 0.25% Arachidonyl-fluoroethylamide in 15% 2-OH-propyl-β-CD | 0 ± 0 | 1.2 ± 0.9 | −0.1 ± 0.8 | −3.6 ± 0.4 | −1.8 ± 1.1 | −1.5 ± 0.6 | −0.7 ± 0.7 |
| *Untreated eye (contralateral)* | | | | | | | |
| 0.9% NaCl | 0 ± 0 | −1.1 ± 0.8 | 1.9 ± 1.7 | 1.1 ± 0.7 | −0.3 ± 1.2 | 1.9 ± 1.3 | 1.9 ± 0.7 |
| 0.25% Arachidonyl-propanolamide in 7.5% in 2-OH-propyl-β-CD | 0 ± 0 | −1.5 ± 2.2 | −2.1 ± 1.7 | 1.2 ± 2.4 | −1.3 ± 2.1 | 1.4 ± 1.1 | −1.2 ± 1.8 |
| 0.25% 8,11,14-Eicosatrienyl-ethanolamide in 7.5% in 2-OH-propyl-β-CD | 0 ± 0 | −0.4 ± 1.3 | 0.6 ± 1.0 | 0.7 ± 0.8 | −0.3 ± 0.8 | −0.7 ± 0.6 | 0.0 ± 1.1 |
| 0.25% 7,10,13,16-Docosatetraenyl-ethanolamide in 7.5% 2-OH-propyl-β-CD | 0 ± 0 | −1.9 ± 1.1 | 0.4 ± 1.2 | −1.1 ± 1.5 | 1.0 ± 1.6 | −1.8 ± 1.7 | −0.4 ± 1.0 |
| 0.25% Arachidonyl-fluoroethylamide in 10% 2-OH-propyl-β-CD | 0 ± 0 | −0.5 ± 0.9 | −1.1 ± 1.0 | 0.1 ± 1.3 | −0.3 ± 0.6 | 0.6 ± 0.7 | −0.1 ± 0.5 |
| 0.25% Arachidonyl-ethanethiolamide in 15% 2-OH-propyl-β-CD | 0 ± 0 | −2.0 ± 0.6 | −0.9 ± 0.3 | −0.1 ± 1.1 | 0.0 ± 0.0 | −0.6 ± 0.8 | 0.2 ± 1.0 |

As shown in FIG. 7A and Table III above, unilateral ocular administration of arachidonylpropanolamide decreases the IOP in treated eyes in normotensive pigmented rabbits when compared to administration of a 0.9% (w/v) NaCl solution. In the treated eyes of normotensive pigmented rabbits, cyclodextrin vehiculated arachidonylpropanolamide showed a maximal IOP reduction of 3.8 mmHg, 3 hr after 0.25% (w/v) arachidonylpropanolamide treatment.

However, as shown in FIG. 7B and Table III above, unilateral ocular administration of arachidonylpropanolamide does not greatly affect the IOP in the contralateral (untreated) eye in normotensive pigmented rabbits when compared to administration of the 0.9% (w/v) NaCl solution. In the contralateral eye of normotensive pigmented rabbits, the maximal IOP reduction was 2.1 mmHg, 1 hr after 0.25% (w/v) arachidonylpropanolamide treatment.

EXAMPLE 7

In this example, the effect of a 0.25% (w/v) 8,11,14-eicosatrienylethanolamide solution on IOP of normotensive pigmented rabbits weighing between 2.6–3.6 kg (n=6) was studied. The rabbits were housed separately in cages under standard laboratory conditions, i.e., 10 hr dark/14 hr light cycle.

More specifically, 12.5 mg of 8,11,14-eicosatrienylethanolamide and 375 mg of 2-OH-propyl-β-CD were added to distilled water, and the solution was adjusted to pH 7.0 with sodium hydroxide/hydrochloric acid. Then, distilled water was added to adjust the total volume to 5.0 ml. The osmolality of the solution was adjusted to isotonic, 309 mOsm/kg, with sodium chloride.

As a control, a 0.9% (w/v) NaCl was also prepared.

Then, 25 μl of either the drug-CD solution or the NaCl solution was administered unilaterally to the rabbits. The rabbits were kept in restraint boxes during the study.

IOP was measured using a BioRad (Cambridge, Mass.) Digilab Modular One Pneumatonometer. Before each measurement, one or two drops of 0.06% (w/v) oxybuprocaine were applied to the cornea as an anaesthetic before tonometry to eliminate discomfort. For each determination, at least two readings were taken from each eye. The measurements were started 2 hr before drug-CD or 0.9% (w/v) NaCl solution administration, and were continued for 5 hr after administration.

The IOPs of the pigmented rabbits at the time of eyedrop administration were between 15.0–22.5 mmHg (n=6).

Figure 8A:
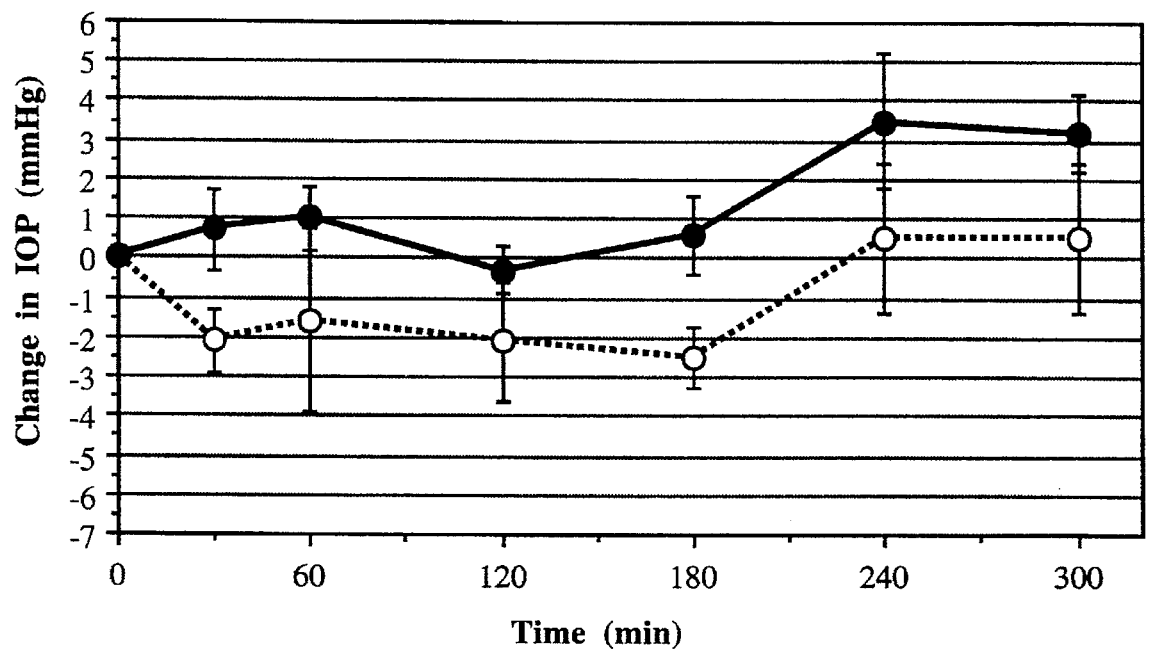
FIG. 8A shows the IOP changes in normotensive pigmented rabbits (treated eyes) after unilateral ocular administration (25 μl) of 0.25% (w/v) 8,11,14-eicosatrienylethanolamide (o) or 0.9% (w/v) NaCl (●), means ± S.E. (n=6).
Figure 8B:
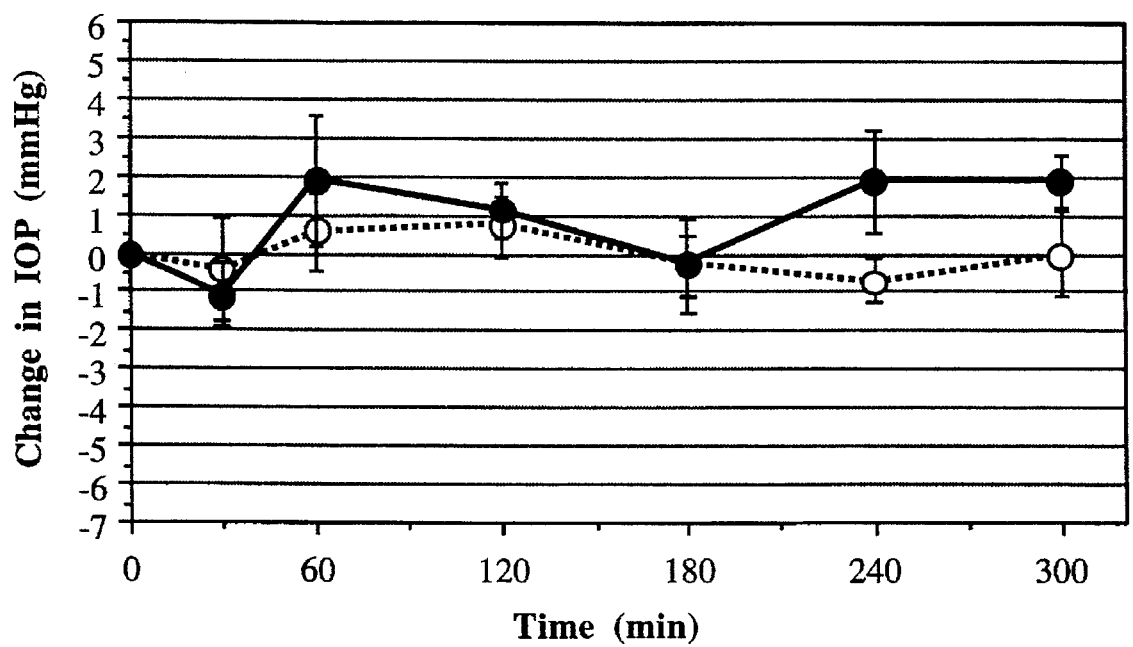
FIG. 8B shows the IOP changes in normotensive pigmented rabbits (untreated eyes) after unilateral ocular administration (25 μl) of 0.25% (w/v) 8,11,14-eicosatrienylethanolamide (o) or 0.9% (w/v) NaCl (●), means ± S.E. (n=6).

The results are shown in FIGS. 8A and 8B, and Table III below. All of the values are expressed as the mean ± standard error of means (X ± S.E.).

As shown in FIG. 8A and Table III above, unilateral ocular administration of 8,11,14-eisosatrienylethanolamide decreases the IOP in treated eyes in normotensive pigmented rabbits when compared to administration of a 0.9% (w/v) NaCl solution. In the treated eyes of normotensive pigmented rabbits, cyclodextrin vehiculated 8,11,14-eicosatrienylethanolamide showed a maximal IOP reduction of 2.5 mmHg, 3 hr after 0.25% (w/v) 8,11,14-eicosatrienylethanolamide treatment.

However, as shown in FIG. 8B and Table III above, unilateral ocular administration of 8,11,14-eicosatrienylethanolamide does not greatly affect the IOP in the contralateral (untreated) eye in normotensive pigmented rabbits when compared to administration of the 0.9% (w/v) NaCl solution. In the contralateral eye of normotensive pigmented rabbits, the maximal IOP reduction was 0.7 mmHg, 4 hr after 0.25% (w/v) 8,11,14-eicosatrienylethanolamide treatment.

EXAMPLE 8

In this example, the effect of a 0.25% (w/v) 7,10,13,16-docosatetraenylethanolamide solution on IOP of normotensive pigmented rabbits weighing between 2.6–3.6 kg (n=6) was studied. The rabbits were housed separately in cages under standard laboratory conditions, i.e., 10 hr dark/14 hr light cycle.

More specifically, 12.5 mg of 7,10,13,16-docosatetraenylethanolamide and 375 mg of 2-OH-propyl-β-CD were added to distilled water, and the solution was adjusted to pH 7.0 with sodium hydroxide/hydrochloric acid. Then, distilled water was added to adjust the total volume to 5.0 ml. The osmolality of the solution was adjusted to isotonic, 307 mOsm/kg, with sodium chloride.

As a control, a 0.9% (w/v) NaCl was also prepared.

Then, 25 μl of either the drug-CD solution or the NaCl solution was administered unilaterally to the rabbits. The rabbits were kept in restraint boxes during the study.

IOP was measured using a BioRad (Cambridge, Mass.) Digilab Modular One Pneumatonometer. Before each measurement, one or two drops of 0.06% (w/v) oxybuprocaine were applied to the cornea as an anaesthetic before tonometry to eliminate discomfort. For each determination, at least two readings were taken from each eye. The measurements were started 2 hr before drug-CD or 0.9% (w/v) NaCl solution administration, and were continued for 5 hr after administration.

The IOPs of the pigmented rabbits at the time of eyedrop administration were between 13.3–25.7 mmHg (n=6).

Figure 9A:
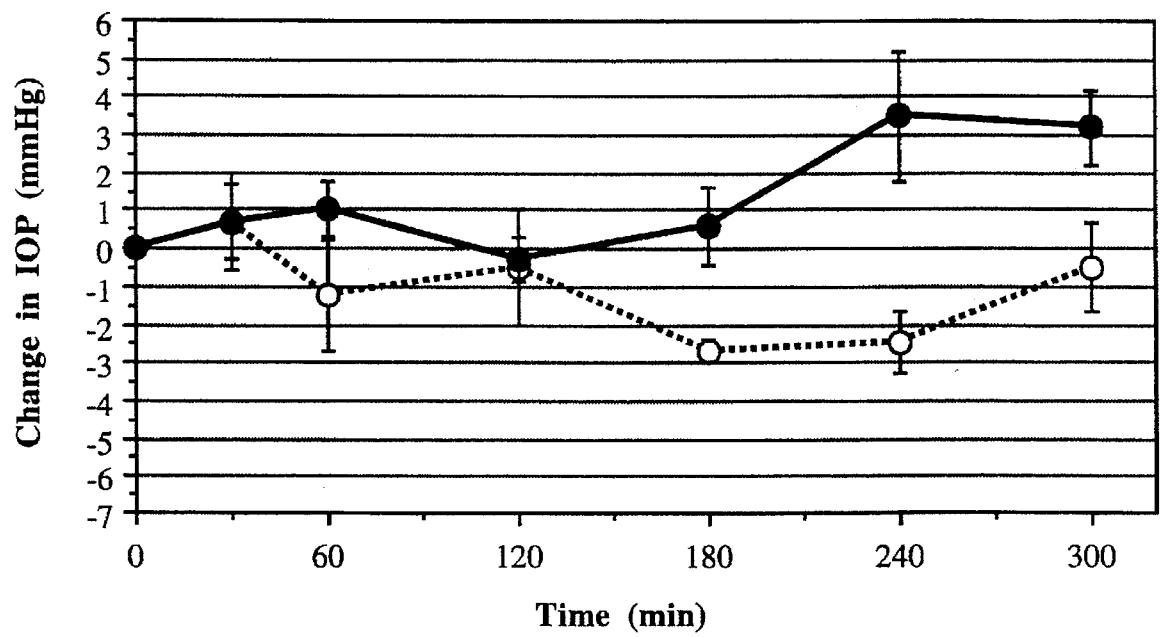
FIG. 9A shows the IOP changes in normotensive pigmented rabbits (treated eyes) after unilateral ocular administration (25 μl) of 0.25% (w/v) 7,10,13,16-docosatetraenylethanolamide (o) or 0.9% (w/v) NaCl (●), mean ± S.E. (n=6).
Figure 9B:
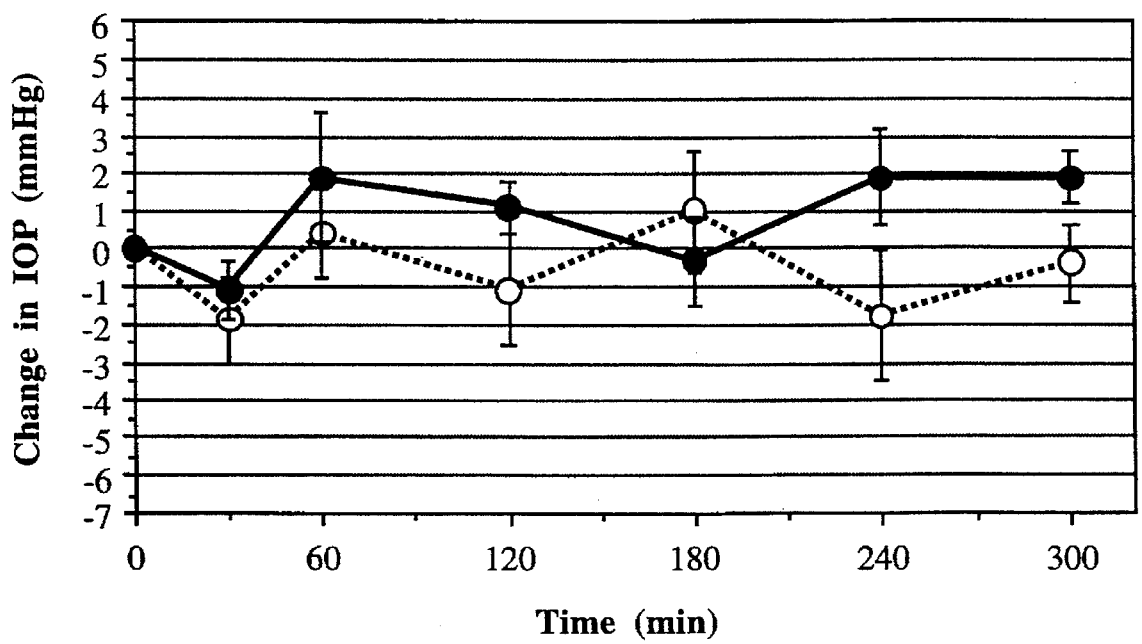
FIG. 9B shows the IOP changes in normotensive pigmented rabbits (untreated eyes) after unilateral ocular administration (25 μl) of 0.25% (w/v) 7,10,13,16-docosatetraenylethanolamide (o) or 0.9% (w/v) NaCl (●), mean ± S.E. (n=6).

The results are shown in FIGS. 9A and 9B, and Table III above. All of the values are expressed as the mean ± standard error of means (X ± S.E.).

As shown in FIG. 9A and Table III above, unilateral ocular administration of 7,10,13,16-docosatetraenylethanolamide decreases the IOP in treated eyes in normotensive pigmented rabbits when compared to administration of a 0.9% (w/v) NaCl solution. In the treated eyes of normotensive pigmented rabbits, cyclodextrin vehiculated 7,10,13,16-docosatetraenylethanolamide showed a maximal IOP reduction of 2.7 mmHg, 3 hr after 0.25% (w/v) 7,10,13,16-docosatetraenylethanolamide treatment.

However, as shown in FIG. 9B and Table III above, unilateral ocular administration of 7,10,13,16-docosatetraenylethanolamide does not greatly affect the IOP in the contralateral (untreated) eye in normotensive pigmented rabbits when compared to administration of the 0.9% (w/v) NaCl solution. In the contralateral eye of normotensive pigmented rabbits, the maximal IOP reduction was 1.9 mmHg, 30 min after 0.25% (w/v) 7,10,13,16-docosatetraenylethanolamide treatment.

EXAMPLE 9

In this example, the effect of a 0.25% (w/v) arachidonylethanethiolamide solution on IOP of normotensive pigmented rabbits weighing between 2.6–3.6 kg (n=5) was studied. The rabbits were housed separately in cages under standard laboratory conditions, i.e., 10 hr dark/14 hr light cycle.

More specifically, 12.5 mg of arachidonylethanethiolamide and 500 mg of 2-OH-propyl-β-CD were added to distilled water, and the solution was adjusted to pH 7.0 with sodium hydroxide/hydrochloric acid. Then, distilled water was added to adjust the total volume to 5.0 ml. The osmolality of the solution was adjusted to isotonic, 325 mOsm/kg, with sodium chloride.

As a control, a 0.9% (w/v) NaCl was also prepared.

Then, 25 μl of either the drug-CD solution or the NaCl solution was administered unilaterally to the rabbits. The rabbits were kept in restraint boxes during the study.

IOP was measured using a BioRad (Cambridge, Mass.) Digilab Modular One Pneumatonometer. Before each measurement, one or two drops of 0.06% (w/v) oxybuprocaine were applied to the cornea as an anaesthetic before tonometry to eliminate discomfort. For each determination, at least two readings were taken from each eye. The measurements were started 2 hr before drug-CD or 0.9% (w/v) NaCl solution administration, and were continued for 5 hr after administration.

The IOPs of the pigmented rabbits at the time of eyedrop administration were between 17.1–27.7 mmHg (n=5).

Figure 10A:
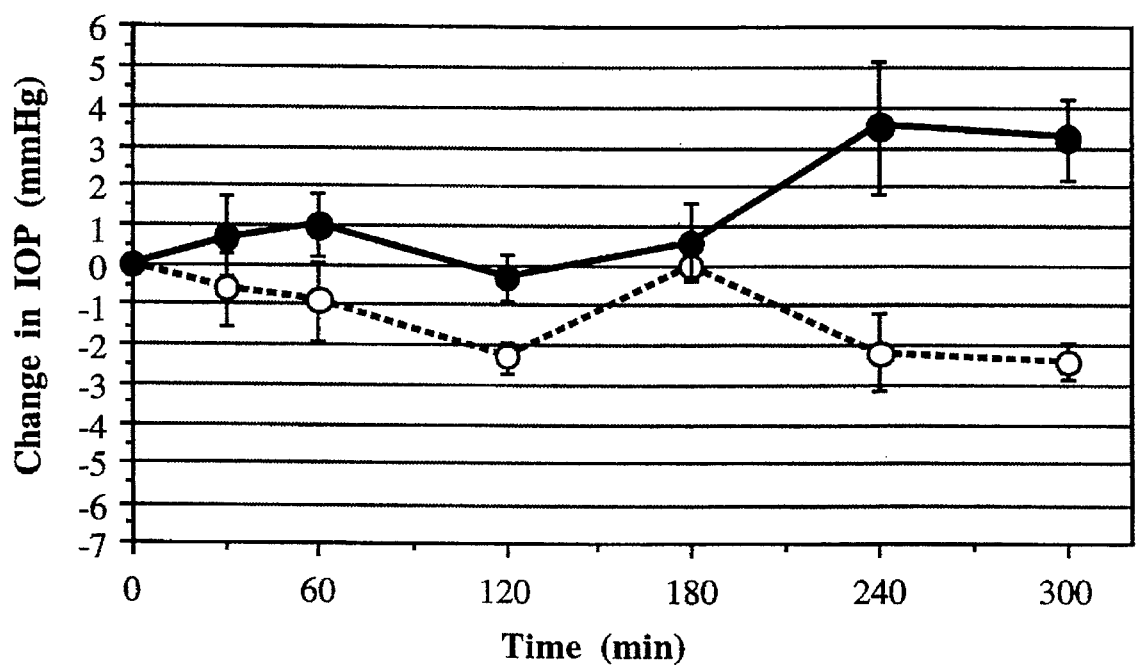
FIG. 10A shows the IOP changes in normotensive pigmented rabbits (treated eyes) after unilateral ocular administration (25 μl) of 0.25% (w/v) arachidonylethanethiolamide (o) or 0.9% (w/v) NaCl (●), means ± S.E. (n=5).
Figure 10B:
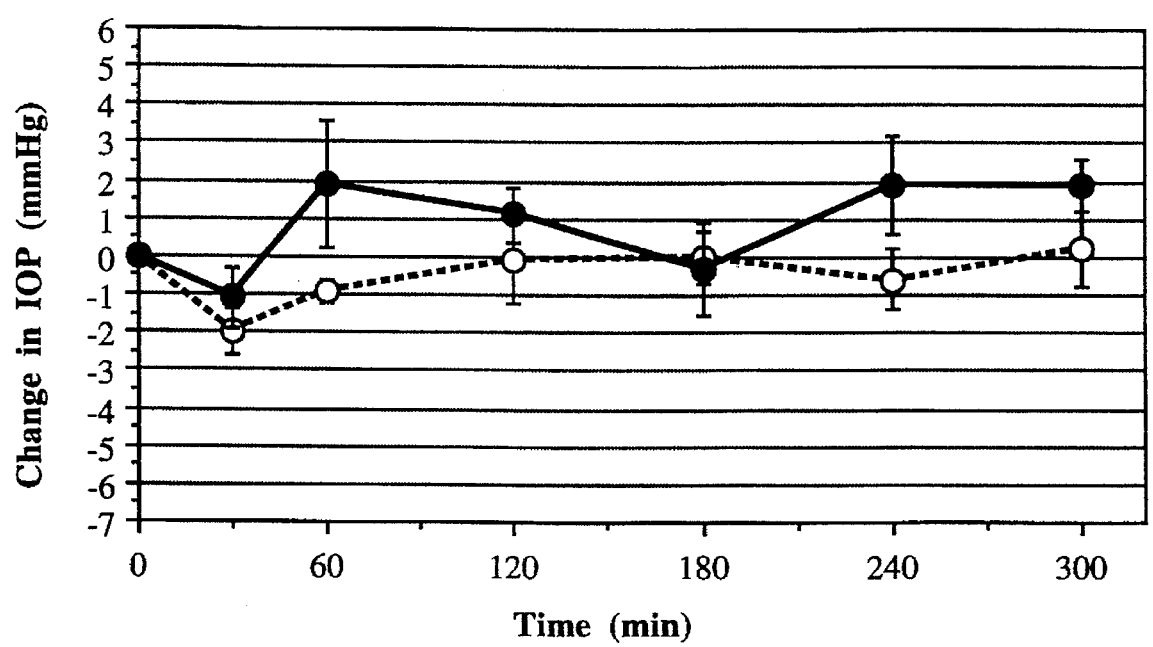
FIG. 10B shows the IOP changes in normotensive pigmented rabbits (untreated eyes) after unilateral ocular administration (25 μl) of 0.25% (w/v) arachidonylethanethiolamide (o) or 0.9% (w/v) NaCl (●), means ± S.E. (n=5).

The results are shown in FIGS. 10A and 10B, and Table III above. All of the values are expressed as mean ± standard error of means (X ± S.E.).

As shown in FIG. 10A and Table III above, unilateral ocular administration of arachidonylethanethiolamide decreases the IOP in treated eyes in normotensive pigmented rabbits when compared to administration of a 0.9% (w/v) NaCl solution. In the treated eyes of normotensive pigmented rabbits, cyclodextrin vehiculated arachidonylethanethiolamide showed a maximal IOP reduction of 2.4 mmHg, 5 hr after 0.25% (w/v) arachidonylethanethiolamide treatment.

However, as shown in FIG. 10B and Table III above, unilateral ocular administration does not greatly affect the IOP in the contralateral (untreated) eye in normotensive pigmented rabbits when compared to administration of the 0.9% (w/v) NaCl solution. In the contralateral eye of normotensive pigmented rabbits, the maximal IOP reduction was 2.0 mmHg, 30 min after 0.25% (w/v) arachidonylethanethiolamide treatment.

EXAMPLE 10

In this example, the effect of a 0.25% (w/v) arachidonylfluoroethylamide solution on IOP of normotensive pigmented rabbits weighing between 2.6–3.6 kg (n=6) was studied. The rabbits were housed separately in cages under standard laboratory conditions, i.e., 10 hr dark/14 hr light cycle.

More specifically, 12.5 mg of arachidonylfluoroethylamide and 750 mg of 2-OH-propyl-β-CD were added to distilled water, and the solution was adjusted to pH 7.0 with sodium hydroxide/hydrochloric acid. Then, distilled water was added to adjust the total volume to 5.0 ml. The osmolality of the solution was adjusted to isotonic, 310 mOsm/kg, with sodium chloride.

As a control, a 0.9% (w/v) NaCl was also prepared.

Then, 25 μl of either the drug-CD solution or the NaCl solution was administered unilaterally to the rabbits. The rabbits were kept in restraint boxes during the study.

IOP was measured using a BioRad (Cambridge, Mass.) Digilab Modular One Pneumatonometer. Before each measurement, one or two drops of 0.06% (w/v) oxybuprocaine were applied to the cornea as an anaesthetic before tonometry to eliminate discomfort. For each determination, at least two readings were taken from each eye. The measurements were started 2 hr before drug-CD or 0.9% (w/v) NaCl solution administration, and were continued for 5 hr after administration.

The IOPs of the pigmented rabbits at the time of eyedrop administration were between 15.2–21.6 mmHg (n=6).

Figure 11A:
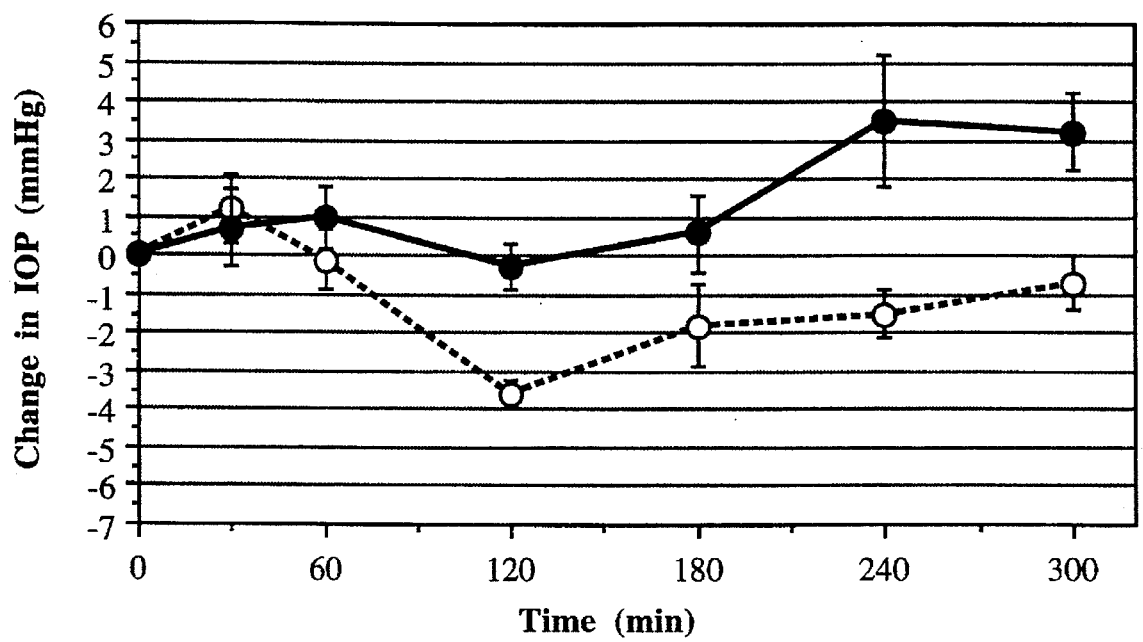
FIG. 11A shows the IOP changes in normotensive pigmented rabbits (treated eyes) after unilateral ocular administration (25 μl) of 0.25% (w/v) arachidonylfluoroethylamide (o) or 0.9% (w/v) NaCl (●), means ± S.E. (n=6).
Figure 11B:
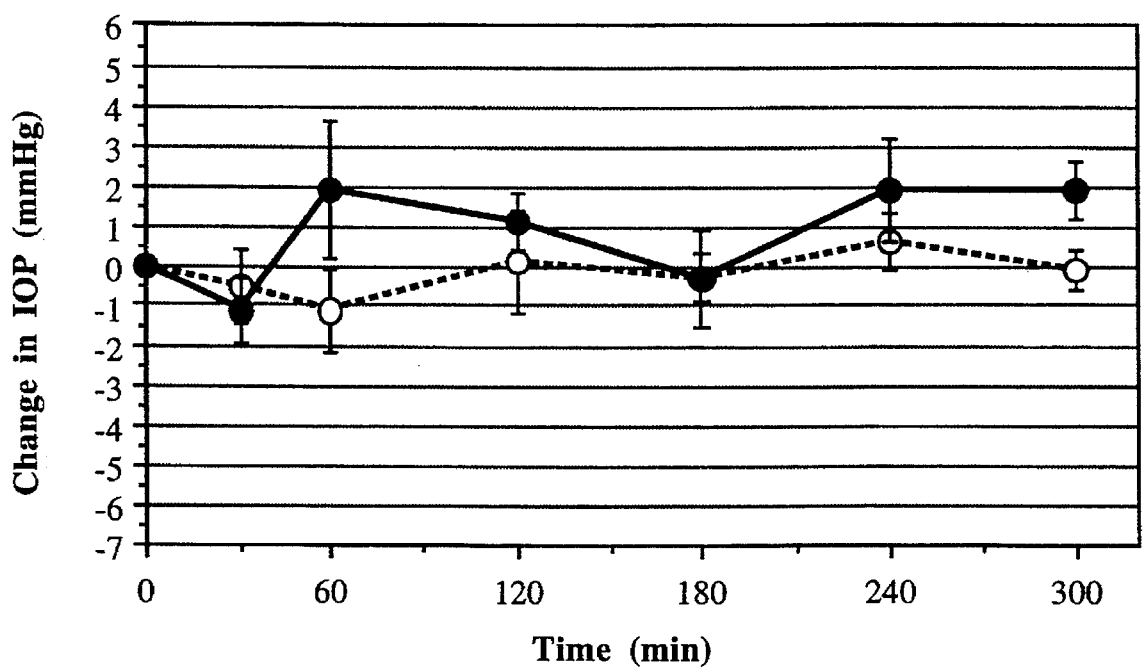
FIG. 11B shows the IOP changes In normotensive pigmented rabbits (untreated eyes) after unilateral ocular administration (25 μl) of 0.25% (w/v) arachidonylfluoroethylamide (o) or 0.9% (w/v) NaCl (●), means ± S.E. (n=5).

The results are shown in FIGS. 11A and 11B, and Table III above. All of the values are expressed as mean ± standard error of means (X ± S.E.).

As shown in FIG. 11A and Table III above, unilateral ocular administration of arachidonylfluoroethylamide decreases the IOP in treated eyes in normotensive pigmented rabbits when compared to administration of a 0.9% (w/v) NaCl solution. In the treated eyes of normotensive pigmented rabbits, cyclodextrin vehiculated arachidonylfluoroethylamide showed a maximal IOP reduction of 3.6 mmHg, 2 hr after 0.25% (w/v) arachidonylfluoroethylamide treatment.

However, as shown in FIG. 11B and Table III above, unilateral ocular administration does not greatly affect the IOP in the contralateral (untreated) eye in normotensive pigmented rabbits when compared to administration of the 0.9% (w/v) NaCl solution. In the contralateral eye of normotensive pigmented rabbits, the maximal IOP reduction was 1.1 mmHg, 60 min after 0.25% (w/v) arachidonylfluoroethylamide treatment.

EXAMPLE 11

In this example, the effect of a 0.25% (w/v) arachidonylethanolamide solution co-administered with heptakis-(2,6-di-O-methyl)-β-CD on IOP of normotensive pigmented rabbits weighing between 2.6–3.6 kg (n=6) was studied. The rabbits were housed separately in cages under standard laboratory conditions, i.e., 10 hr dark/14 hr light cycle.

More specifically, 12.5 mg of arachidonylethanolamide and 125 mg of heptakis-(2,6-di-O-methyl)-β-CD were added to distilled water, and the solution was adjusted to pH 7.0 with sodium hydroxide/hydrochloric acid. Then, distilled water was added to adjust the total volume to 5.0 ml. The osmolality of the solution was adjusted to isotonic, 306 mOsm/kg, with sodium chloride.

As a control, a 0.9% (w/v) NaCl was also prepared.

Then, 25 μl of either the drug-CD solution or the NaCl solution was administered unilaterally to the rabbits. The rabbits were kept in restraint boxes during the study.

IOP was measured using a BioRad (Cambridge, Mass.) Digilab Modular One Pneumatonometer. Before each measurement, one or two drops of 0.06% (w/v) oxybuprocaine were applied to the cornea as an anaesthetic before tonometry to eliminate discomfort. For each determination, at least two readings were taken from each eye. The measurements were started 2 hr before drug-CD or 0.9% (w/v) NaCl solution administration, and were continued for 5 hr after administration.

The IOPs of the pigmented rabbits at the time of eyedrop administration were between 17.4–27.0 mmHg (n=6).

Figure 12A:
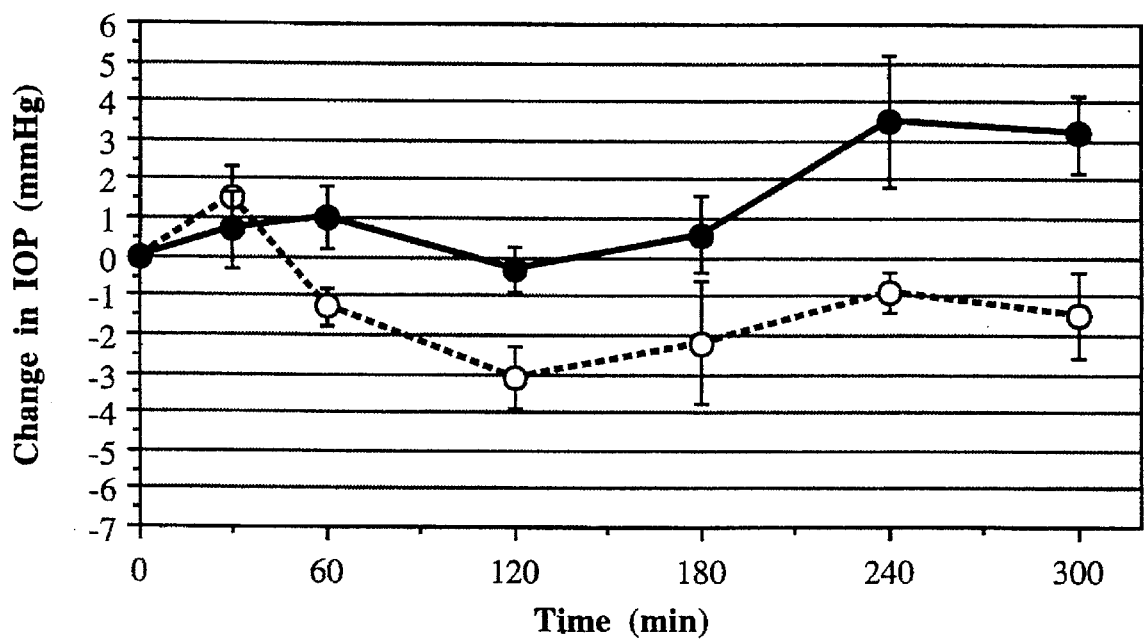
FIG. 12A shows the IOP changes in normotensive pigmented rabbits (treated eyes) after unilateral ocular administration (25 μl) of 0.25% (w/v) arachidonylethanolamide with heptakis-(2,6-di-O-methyl)-β-cyclodextrin (o) or 0.9% (w/v) NaCl (●), means ± S.E. (n=6).
Figure 12B:
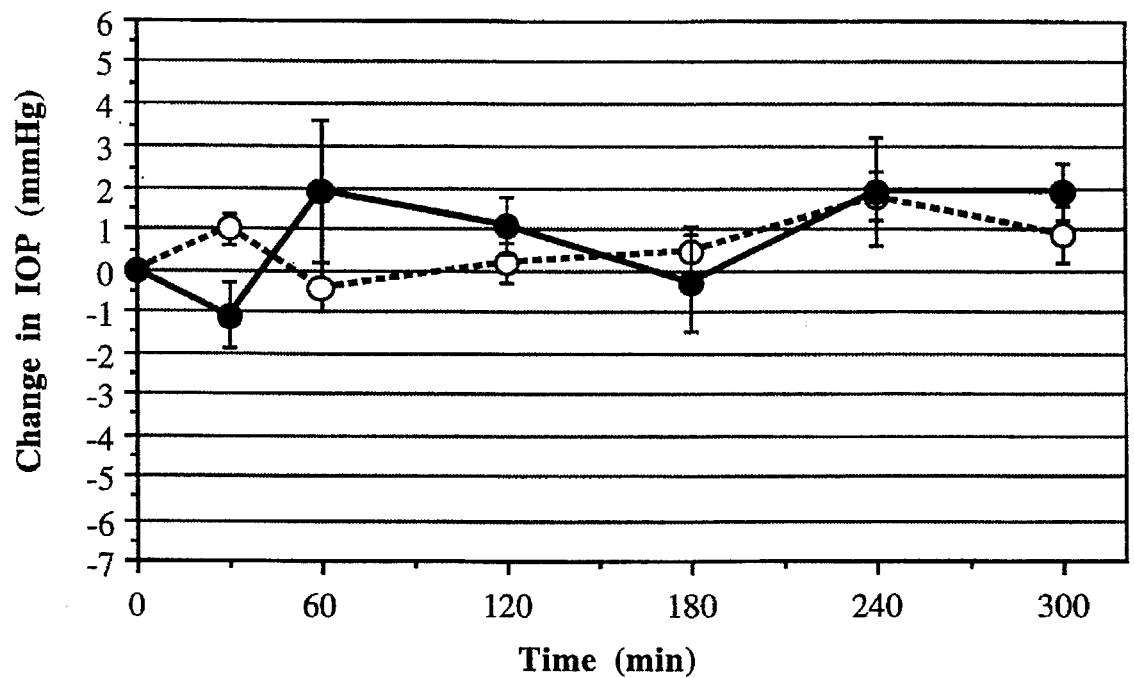
FIG. 12B shows the IOP changes in normotensive pigmented rabbits (untreated eyes) after unilateral ocular administration (25 μl) of 0.25% (w/v) arachidonylethanolamide with heptakis-(2,6-di-O-methyl)-β-cyclodextrin (o) or 0.9% (w/v) NaCl (●), means ± S.E. (n=6).

The results are shown in FIGS. 12A and 12B, and Table I above. All of the values are expressed as mean ± standard error of means (X ± S.E.).

As shown in FIG. 12A and Table III above, unilateral ocular administration of arachidonylethanolamide co-administered with heptakis-(2,6-di-O-methyl)-β-CD decreases the IOP in treated eyes in normotensive pigmented rabbits when compared to administration of a 0.9% (w/v) NaCl solution. In the treated eyes of normotensive pigmented rabbits, heptakis-(2,6-di-O-methyl)-β-CD vehiculated arachidonylethanolamide showed a maximal IOP reduction of 3.1 mmHg, 2 hr after 0.25% (w/v) anandamide treatment.

However, as shown in FIG. 12B and Table III above, unilateral ocular administration of arachidonylethanolamide does not greatly affect the IOP in the contralateral (untreated) eye in normotensive pigmented rabbits when compared to administration of the 0.9% (w/v) NaCl solution. In the contralateral eye of normotensive pigmented rabbits, the maximal IOP reduction was 0.4 mmHg, 1 hr after 0.25% (w/v) arachidonylethanolamide treatment.

The results in the foregoing examples clearly demonstrate that unilateral intraocular administration of an anandamide represented by Formula (I), such as arachidonylethanolamide, 7,10,13,16-docosatetraenylethanolamide, 8,11,14-eicosatrienylethanolamide, arachidonylpropanolamide, arachidonylethanethiolamide and arachidonylfluoroethylamide decreases the IOP in treated eyes in normotensive pigmented (FIGS. 1A, 2A, 7A, 8A, 9A, 10A, 11A and 12A; and Tables I and III) and albino rabbits (FIGS. 3A and Table II) when compared to administration of the 0.9% (w/v) NaCl solution. In the treated eyes of normotensive pigmented rabbits, cyclodextrin vehiculated arachidonylethanolamide showed a maximal IOP reduction of 3.5 mmHg, 1 hr after 0.125% (w/v) arachidonylethanolamide treatment, and maximal IOP reduction of 5.2 mmHg, 2 hr after 0.25% (w/v) arachidonylethanolamide treatment. The maximal IOP reduction in normotensive albino rabbits was 4.4 mmHg, 2 hr after 0.25% (w/v) arachidonylethanolamide treatment.

These results also show that unilateral intraocular administration of anandamides represented by Formula (I) do not greatly affect the IOP in the contralateral eye in normotensive pigmented (FIGS. 1B, 2B, 7B, 8B, 9B, 10B, 11B and 12B; and Tables I and III) and albino rabbits (FIG. 3B and Tables II) when compared to administration of the 0.9% (w/v) NaCl solution. In the contralateral eye of normotensive pigmented and albino rabbits, the maximal IOP reduction was between 0.4 mmHg–2.1 mmHg, 0.5 to 4 hr after treatment with 0.125%–0.25% (w/v) of anandamides represented by Formula (I).

Furthermore, these results show that the unilateral ocular administration of 2-OH-propyl-β-cyclodextrin (5% (w/v), 12.5% (w/v) and 30% (w/v)) alone does not affect the IOP of treated or untreated (contralateral) eyes in normotensive rabbits (FIGS. 4A, 4B, 5A, 5B, 6A and 6B; and Tables I and II) when compared to administration of the 0.9% (w/v) NaCl solution.

Moreover, the results show that with cyclodextrins it is possible to achieve effective ocular delivery of very lipophilic and water-insoluble compounds, like anandamides, from aqueous eye drop formulations. The cyclodextrins increase the ocular bioavailability of anandamides by increasing the aqueous solubility of anandamides in solution and in the tear-fluid on the precorneal area. The concentration and type of cyclodextrin in the composition of the present invention can be readily selected according to a concentration and type of anandamide employed.

Accordingly, based on the foregoing results, it is apparent that anandamides represented by Formula (I), such as arachidonylethanolamide, 7,10,13,16-docosatetraenylethanolamide, 8,11,14-eicosatrienylethanolamide and arachidonylpropanolamide, arachidonylethanethiolamide and arachidonylfluoroethylamide, appear to act locally within the treated eye, perhaps via a specific receptor, rather than systemically (the central nervous system). This is because unilateral ocular administration of the compounds represented by Formula (I) do not greatly affect the IOP in the contralateral, or untreated eye.

Although the mechanism of action by which anandamides represented by Formula (I) produce their hypotensive effect in the eye is not entirely understood, these results indicate that they are promising drugs for treatment of intraocular hypertension. The results also indicate that the cyclodextrin vehiculated anandamides are suitable for topical ocular administration.

While the invention has been described in detail, and with reference to specific embodiments thereof, it will be apparent to one of ordinary skill in the art that various changes and modifications can be made therein without departing from the spirit and scope thereof.

What is claimed is:

1. An ophthalmic composition for reducing intraocular pressure comprising an admixture of:

(A) a pharmaceutically effective amount of an anandamide represented by Formula (I):

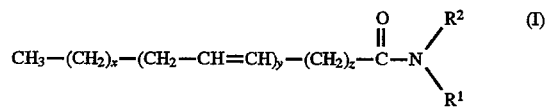

wherein
$R^1$ and $R^2$ are each H or $(CH_2)_a\text{-}(R^4CH)_b\text{—}(CH_2)_c\text{-}R^3$, wherein a, b and c are each an integer of from 0 to 10; and $R^3$ is OH, SH, $CH_3$, $CH=CH_2$, $C\equiv CH$, $C\equiv N$, F, Cl, Br or I; $R^4$ is H or $(CH_2)_l\text{—}CH_3$, wherein l is an integer from 0 to 10; provided that $a+b+c+l\leq 10$;
x is an integer of from 0 to 18;
y is an integer of from 0 to 8;
z is an integer of from 0 to 18; and
(B) a cyclodextrin.

2. The ophthalmic composition according to claim 1, wherein said anandamide is selected from the group consisting of arachidonylethanolamide, arachidonylethanethiolamide, arachidonylfluoroethylamide, arachidonylpropanolamide, 8,11,14-eicosatrienylethanolamide, 7,10,13,16-docosatetraenylethanolamide, palmatidylethanolamide, 4,7,10,13,16,19-docosahexaenylethanolamide, arachidylfluoroethylamide, arachidonylamide, arachidonyl-1-methyl-ethanolamide, arachidonyl-2-methyl-ethanolamide, gamma-linolenylethanolamide and linoleylethanolamide.

3. The ophthalmic composition according to claim 1, wherein said cyclodextrin is 2-hydroxypropyl-β-cyclodextrin or heptakis-(2,6-O-methyl)-β-cyclodextrin.

4. The ophthalmic composition according to claim 1, wherein said ophthalmic composition is an aqueous solution containing 0.01 to 2.0% (w/v) of said anandamide represented by Formula (I), and 0.5 to 40% (w/v) of a cyclodextrin.

5. The ophthalmic composition according to claim 4, wherein said ophthalmic composition is an aqueous solution containing 0.1 to 0.5% (w/v) of said anandamide represented by Formula (I), and 1.0 to 15% (w/v) of a cyclodextrin.

6. The ophthalmic composition according to claim 4, wherein the composition further comprises a water-soluble polymeric compound as a viscosity enhancing agent.

7. The ophthalmic composition according to claim 6, wherein said water-soluble polymeric compound is selected from the group consisting of hydroxypropylmethyl cellulose, hydroxyethyl cellulose, hydroxypropyl cellulose, methyl cellulose, polyvinyl alcohols, sodium polyacrylate, sodium carboxymethyl cellulose, polyvinyl pyrrolidone, hyaluronic acid, and polyacrylic acid.

8. The ophthalmic composition according to claim 7, wherein the viscosity enhancing agent is present in an amount to give a viscosity in the range of 1 to 1,000 cP.

9. The ophthalmic composition according to claim 8, wherein the viscosity enhancing agent is present in an amount to give a viscosity in the range of 5 to 50 cP.

10. The ophthalmic composition according to claim 4, wherein the composition further comprises a buffering agent.

11. The ophthalmic composition according to claim 10, wherein said buffering agent is selected from the group consisting of acetate, citrate, phosphate, borate buffers, and a mixture thereof.

12. The ophthalmic composition according to claim 11, wherein the concentration of the buffering agent is about 1.0 mM to 200 mM.

13. The ophthalmic composition according to claim 12, wherein the concentration of the buffering agent is about 10 mM to 100 mM.

14. The ophthalmic composition according to claim 10, wherein the solution has a pH in the range of 4.0 to 8.0.

15. A method for the treatment of intraocular hypertension, comprising topically administering to an eye of a subject in need of such treatment, a pharmaceutically effective amount of an anandamide represented by Formula (I):

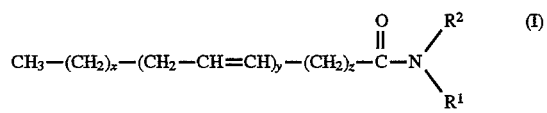

wherein $R^1$ and $R^2$ are each H or $(CH_2)_a\text{-}(R^4CH)_b\text{—}(CH_2)_c\text{-}R^3$, wherein a, b and c are each an integer of from 0 to 10; and $R^3$ is OH, SH, $CH_3$, $CH=CH_2$, $C\equiv CH$, $C\equiv N$, F, Cl, Br or I; $R^4$ is H or $(CH_2)_l$—$CH_3$, wherein l is an integer from 0 to 10; provided that $a+b+c+l \leq 10$;

x is an integer of from 0 to 18;

y is an integer of from 0 to 8; and z is an integer of from 0 to 18.

16. The method according to claim 15, wherein said anandamide is selected from the group consisting of arachidonylethanolamide, arachidonylethanethiolamide, arachidonylfluoroethylamide, arachidonylpropanolamide, 8,11,14-eicosatrienylethanolamide, 7,10,13,16-docosatetraenylethanolamide, palmatidylethanolamide, 4,7,10,13,16,19-docosahexaenylethanolamide, arachidylfluoroethylamide, arachidonylamide, arachidonyl-1-methyl-ethanolamide, arachidonyl-2-methyl-ethanolamide, gamma-linolenylethanolamide and linoleylethanolamide.

17. The method according to claim 15, wherein said anandamide represented by Formula (I) is administered as an admixture with a cyclodextrin.

18. The method according to claim 17, wherein said cyclodextrin is 2-hydroxypropyl-β-cyclodextrin or heptakis-(2,6-O-methyl)-β-cyclodextrin.

19. The method according to claim 17, wherein said admixture is an aqueous solution containing 0.01 to 2.0% (w/v) of said anandamide represented by Formula (I), and 0.5 to 40% (w/v) of a cyclodextrin.

20. The method according to claim 19, wherein said admixture is an aqueous solution containing 0.1 to 0.5% (w/v) of said anandamide represented by Formula (I), and 1.0 to 15% (w/v) of a cyclodextrin.

21. The method according to claim 17, wherein the admixture further comprises a water-soluble polymeric compound as a viscosity enhancing agent.

22. The method according to claim 21, wherein said water-soluble polymeric compound is selected from the group consisting of hydroxypropylmethyl cellulose, hydroxyethyl cellulose, hydroxypropyl cellulose, methyl cellulose, polyvinyl alcohols, sodium polyacrylate, sodium carboxymethyl cellulose, polyvinyl pyrrolidone, hyaluronic acid, and polyacrylic acid.

23. The method according to claim 21, wherein the viscosity enhancing agent is present in an amount to give a viscosity in the range of 1 to 1,000 cP.

24. The method according to claim 23, wherein the viscosity enhancing agent is present in an amount to give a viscosity in the range of 5 to 50 cP.

25. The method according to claim 17, wherein the admixture further comprises a buffering agent.

26. The method according to claim 25, wherein said buffering agent is selected from the group consisting of acetate, citrate, phosphate, borate buffers, and a mixture thereof.

27. The method according to claim 25, wherein the concentration of the buffering agent is about 1.0 mM to 200 mM.

28. The method according to claim 27, wherein the concentration of the buffering agent is about 10 mM to 100 mM.

29. The method according to claim 25, wherein the admixture has a pH in the range of 4.0 to 8.0.

* * * * *